(12) United States Patent
Lewis et al.

(10) Patent No.: US 10,878,942 B2
(45) Date of Patent: Dec. 29, 2020

(54) PERPETUAL BIOINFORMATICS AND VIRTUAL COLORIMETER EXPERT SYSTEM

(71) Applicants: Gregory Edward Lewis, Pittsford, NY (US); Charles Geiger, San Jose, CA (US)

(72) Inventors: Gregory Edward Lewis, Pittsford, NY (US); Charles Geiger, San Jose, CA (US)

( * ) Notice: Subject to any disclaimer, the term of this patent is extended or adjusted under 35 U.S.C. 154(b) by 144 days.

(21) Appl. No.: 16/051,444

(22) Filed: Jul. 31, 2018

(65) Prior Publication Data

US 2019/0080052 A1 Mar. 14, 2019

Related U.S. Application Data

(63) Continuation of application No. 15/976,840, filed on May 10, 2018.
(Continued)

(51) Int. Cl.
*G06T 3/00* (2006.01)
*G06T 7/33* (2017.01)
(Continued)

(52) U.S. Cl.
CPC ............ *G16B 45/00* (2019.02); *A61B 5/0077* (2013.01); *A61B 5/1032* (2013.01);
(Continued)

(58) Field of Classification Search
CPC ...... G16B 45/00; G16B 40/00; G06K 9/2018; G06K 9/6215; G06K 9/4652; A61B 5/1032; A61B 5/441; A61B 5/448; A61B 5/1034; A61B 5/0077; A61B 5/7425; A61B 5/015; A61B 5/4854; A61B 5/7264; G16H 40/67; G16H 30/40; G16H 50/30; G01J 3/465; G01J 3/50; G06T 7/0012; G06T 11/001;
(Continued)

(56) References Cited

U.S. PATENT DOCUMENTS 5,150,199 A * 9/1992 Shoemaker .............. H04N 9/67
345/603
7,262,779 B1 * 8/2007 Sones ........................ G01J 3/02
345/589
(Continued)

*Primary Examiner* — Christopher M Brandt
(74) *Attorney, Agent, or Firm* — Mnemoglyphics, LLC; Lawrence M. Mennemeier

(57) ABSTRACT

A perpetual bioinformatics and virtual colorimeter expert system platform is disclosed to remotely measure dermal and epidermal properties with precision and to enhance decision-making. Some embodiments of the system provide for virtual tristimulus colorimetry, wherein a capture device captures one or more dermal images of one or more skin area of a user. A color grid includes one or more permutations of a plurality of recorded predetermined colors. A scale of the color grid is recorded as being printed or projected at a predetermined size. Application of the virtual tristimulus colorimeter to one of the images is performed. As a result of this application the image is calibrated according to the virtual tristimulus colorimeter. In some embodiments the capture device may include a smartphone camera, interactive with the virtual tristimulus colorimeter smartphone application.

23 Claims, 22 Drawing Sheets

US 10,878,942 B2
Page 2

Related U.S. Application Data

(60) Provisional application No. 62/509,622, filed on May 22, 2017.

(51) Int. Cl.

| | | |
|---|---|---|
| *G16B 45/00* | (2019.01) | |
| *G06K 9/46* | (2006.01) | |
| *A61B 5/00* | (2006.01) | |
| *A61B 5/103* | (2006.01) | |
| *G01J 3/50* | (2006.01) | |
| *G06T 7/00* | (2017.01) | |
| *G06K 9/20* | (2006.01) | |
| *G06K 9/62* | (2006.01) | |
| *G16H 40/67* | (2018.01) | |
| *G16H 30/40* | (2018.01) | |
| *G16H 50/30* | (2018.01) | |
| *G16B 40/00* | (2019.01) | |
| *G01J 3/46* | (2006.01) | |
| *G06T 11/00* | (2006.01) | |
| *G06T 7/90* | (2017.01) | |
| *G06T 11/60* | (2006.01) | |
| *A61B 5/01* | (2006.01) | |

(52) U.S. Cl.
CPC ............ *A61B 5/1034* (2013.01); *A61B 5/441* (2013.01); *A61B 5/448* (2013.01); *A61B 5/7264* (2013.01); *A61B 5/7425* (2013.01); *G01J 3/465* (2013.01); *G01J 3/50* (2013.01); *G06K 9/2018* (2013.01); *G06K 9/4652* (2013.01); *G06K 9/6215* (2013.01); *G06T 7/0012* (2013.01); *G06T 7/0014* (2013.01); *G06T 11/001* (2013.01); *G16B 40/00* (2019.02); *G16H 30/40* (2018.01); *G16H 40/67* (2018.01); *G16H 50/30* (2018.01); *A61B 5/015* (2013.01); *A61B 5/4854* (2013.01); *G06T 7/90* (2017.01); *G06T 11/60* (2013.01); *G06T 2200/24* (2013.01); *G06T 2207/10024* (2013.01); *G06T 2207/10048* (2013.01); *G06T 2207/30088* (2013.01)

(58) Field of Classification Search
CPC ..................... G06T 7/0014; G06T 7/90; G06T 2207/10048; G06T 2200/24; G06T 11/60; G06T 2207/10024; G06T 2207/30088
See application file for complete search history.

(56) References Cited

U.S. PATENT DOCUMENTS

| | | | |
|---|---|---|---|
| 9,068,887 B1* | 6/2015 | Bennouri | G01J 1/429 |
| 2009/0015851 A1* | 1/2009 | Yamaguchi | H04N 1/6033 |
| | | | 358/1.9 |
| 2010/0238300 A1* | 9/2010 | Kojima | G01J 3/46 |
| | | | 348/207.1 |
| 2014/0300753 A1* | 10/2014 | Yin | G01J 3/50 |
| | | | 348/187 |
| 2015/0145884 A1* | 5/2015 | Jang | G01J 3/0264 |
| | | | 345/603 |
| 2015/0317928 A1* | 11/2015 | Safaee-Rad | G09G 3/2003 |
| | | | 345/593 |
| 2016/0234490 A1* | 8/2016 | Sasada | G01J 3/506 |
| 2018/0080829 A1* | 3/2018 | Tanimura | G01J 3/524 |

* cited by examiner

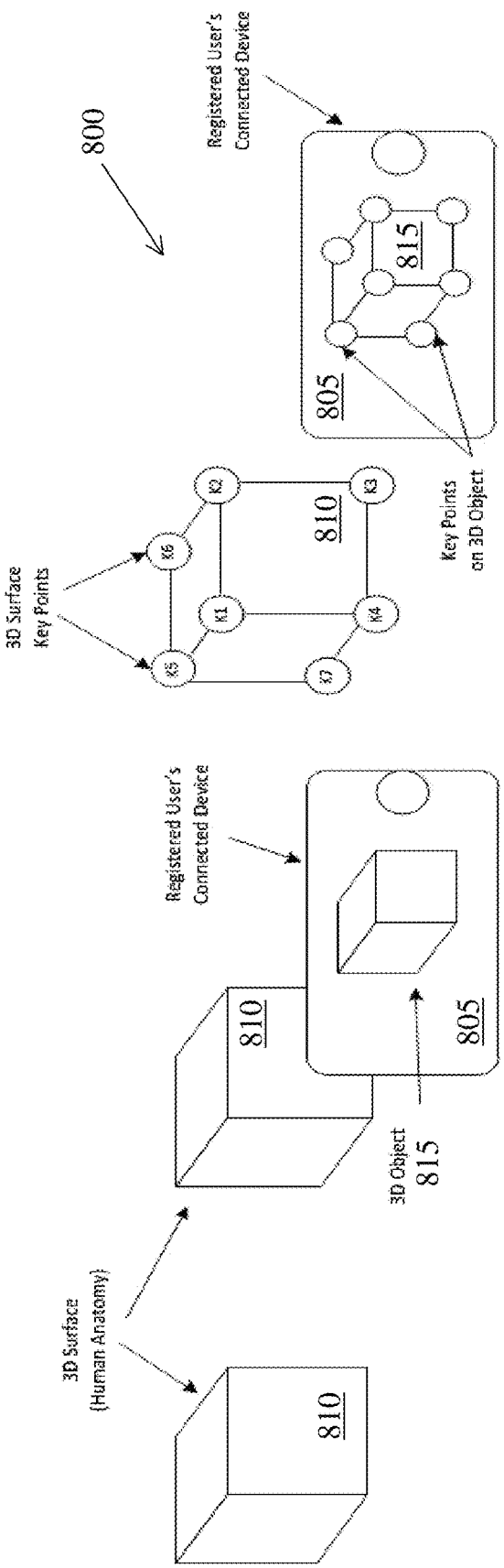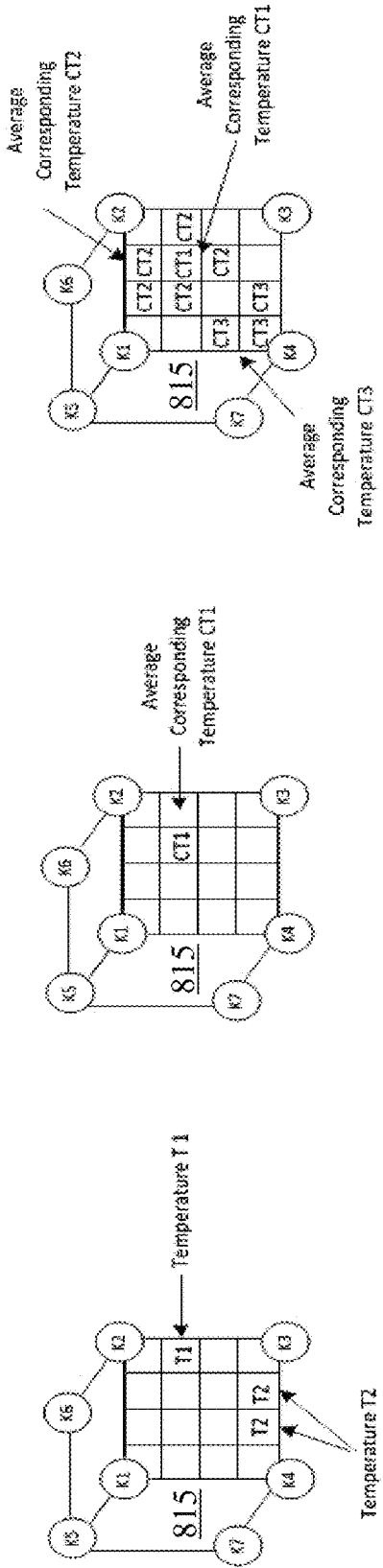
FIG. 8

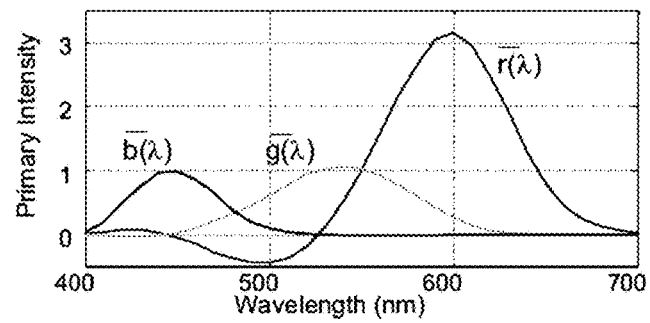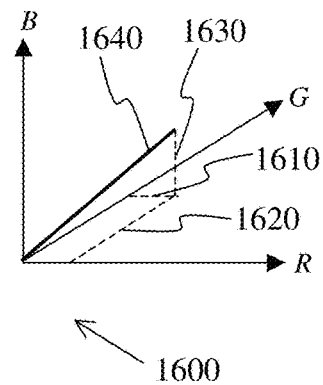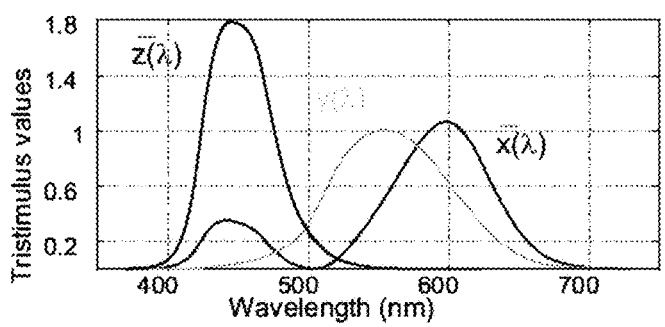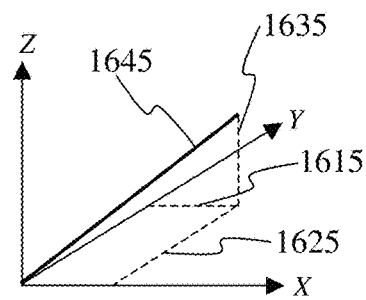
FIG. 16A
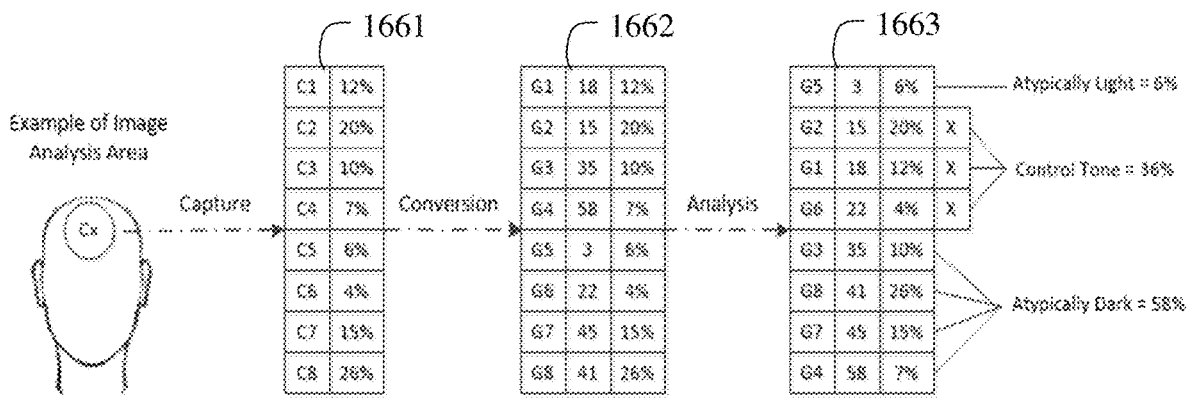
FIG. 16B

Step 1  1732

Through the protocol valuation technique, a prioritization of support is created.

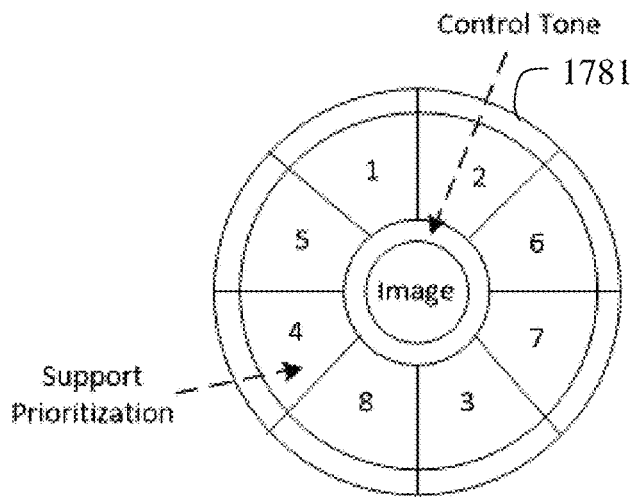

Step 2  1760

Tones designated as control tones are not distributed into sections.

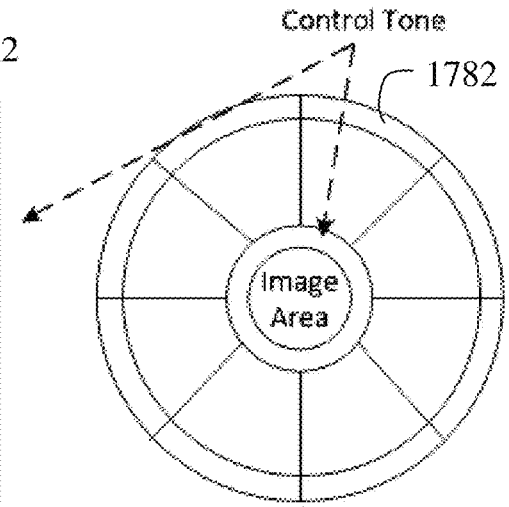

Step 3  1761

The remaining atypical tones are distributed into sections by matching color percentages with priority values with the highest percentage in priority category 1 and succession from there on.

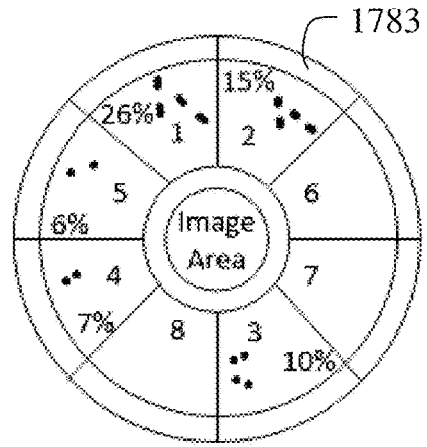

PERPETUAL BIOINFORMATICS AND VIRTUAL COLORIMETER EXPERT SYSTEM

CROSS-REFERENCE TO RELATED APPLICATIONS

This application is a continuation of U.S. patent application Ser. No. 15/976,840 filed May 10, 2018, which claims priority under 35 U.S.C. § 120 to Provisional Patent Application No. 62/509,622, filed May 22, 2017. The entire disclosure of Provisional Patent Application No. 62/509,622 is hereby incorporated herein by reference.

FIELD OF THE DISCLOSURE

This invention generally relates to an expert system. More specifically, the present invention relates to a perpetual bioinformatics and virtual colorimeter expert system platform to remotely measure dermal and epidermal properties with precision and enhance decision-making through expert diagnostic and predictive services.

BACKGROUND OF THE DISCLOSURE

A typical consultation with a dermatologist or other skin-care professional may include an office visit and examination. Optimally, the skin region being analyzed will be free of topical applications and visible hair. But since an office visit is typically scheduled during working hours, clients may come from their own working environment, and may have already applied makeup, etc. Typically consultation with a dermatologist may also potentially include photographic and/or digital imagery, infrared imagery, etc. In such cases, the images may require high resolution and consistent lighting. For example, accurate epidermal tristimulus (3-valued) color images may be captured by a specialized piece of hardware known as a colorimeter, which is designed to filter lighting sources to accurately provide tristimulus values.

In the course of treatments prescribed by a dermatologist or other skin-care professional, implementation by the client of the prescribed treatments, continued monitoring of treated areas by the professional, engagement between the professional and client during the implementation and adjustments to the prescribed treatments, may be crucial to the success of any such course of treatments. But frequent office visits and examinations may become prohibitively expensive, and difficult to schedule into the busy day-to-day routines of both professionals and clients; and subjective evaluations of treatment progress by the client may not be sufficient to motivate continued implementation of, and prompt adjustments to the prescribed treatments.

As a result, client success rates may be lowered due to a lack of adequate support systems that could keep the client motivated and engaged during the time between scheduled sessions with their professional. Human motivation levels can vary significantly as related to the specified time-period considered necessary to achieve an identified goal. Acquisition of new habits necessary for maintaining long term success may also be hindered by barriers that interfere with an effective, efficient and continuous engagement process. These factors can contribute to protracted time requirements for successful treatment, and increased long-term likelihood of failure.

To date, potential solutions to such factors, expenses, scheduling circumstances and/or technical difficulties have not been adequately explored.

BRIEF DESCRIPTION OF THE DRAWINGS

The present invention is illustrated by way of example and not limitation in the figures of the accompanying drawings:

FIGS. 8A, 8B, 8C, 8D, 8E and 8F illustrate one embodiment of a process for asymmetrical and atypical measurements.

FIGS. 16A and 16B illustrate respectively, according to one embodiment of the PBVCES: color distance measurements, both in an example input-device color space, and in an another alternative example color space; and an example process flow of an image area analysis.

FIG. 17 illustrates, according to one embodiment of the PBVCES, a valuation wheel and logic of atypical tone mapping graphics.

DETAILED DESCRIPTION OF THE PREFERRED EMBODIMENTS

Figure 1:
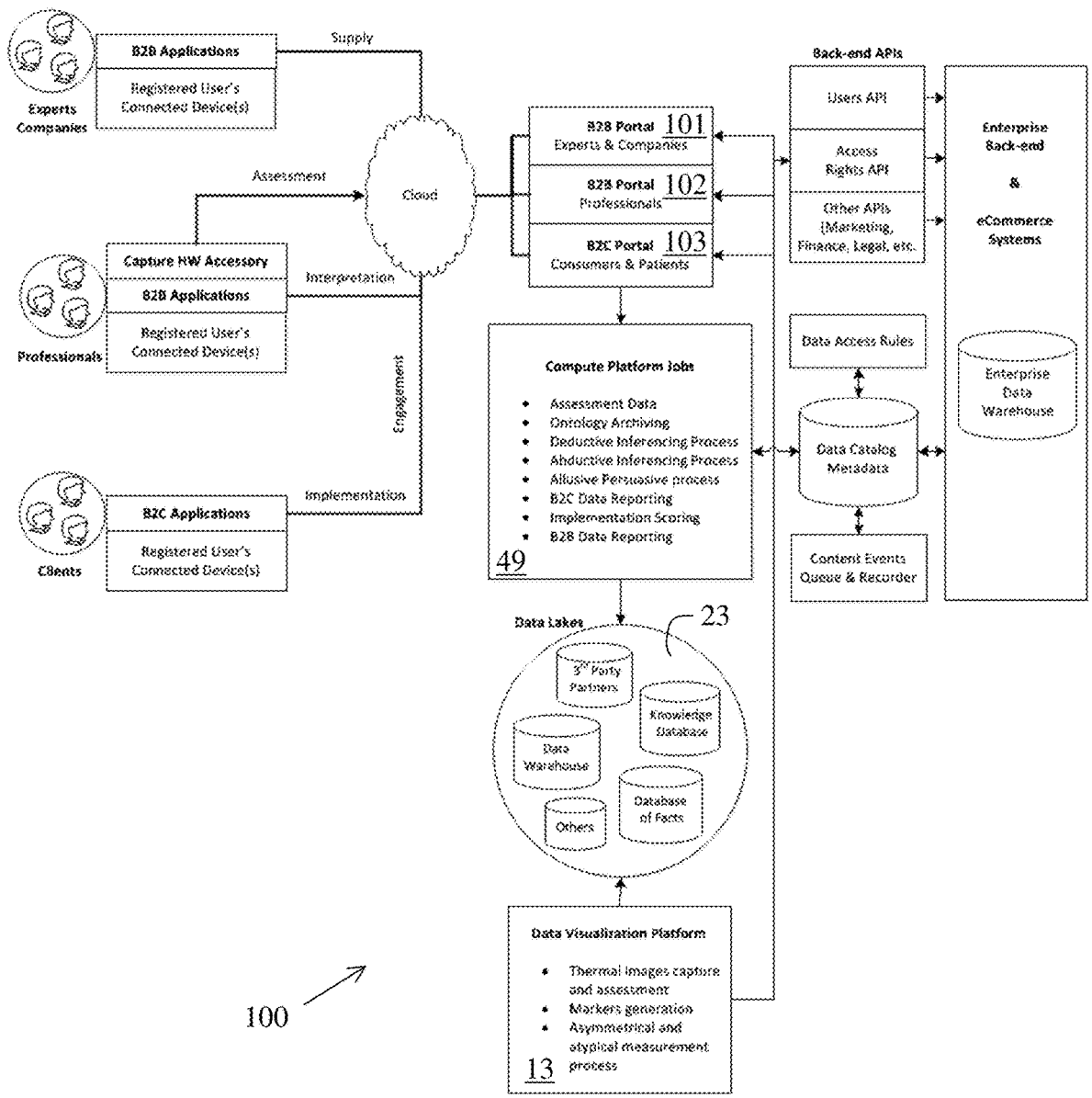
FIG. 1 illustrates one embodiment of a perpetual bioinformatics and virtual colorimeter expert system (PBVCES) platform.

Selected embodiments of the present invention will now be explained with reference to the drawings. It will be apparent to those skilled in the art from this disclosure that the following descriptions of the embodiments of the present invention are provided for illustration only and not for the purpose of limiting the invention as defined by the appended claims and their equivalents.

A perpetual bioinformatics and virtual colorimeter expert system (PBVCES) platform is disclosed below to remotely measure dermal and epidermal properties with precision and to enhance decision-making through artificial intelligence by offering expert diagnostic and predictive services. Some embodiments of the system, which map atypical skin discoloration may include capture means for capturing dermal images of the skin area of a user to be evaluated; control means for identifying the control tone area of a user based on conditional parameters; classification means for classifying the discoloration tones from captured dermal images; measurement means for measuring discoloration tones outside the spectrum of standardized normal tones; and quantification means for calculating the ratio of severity of tone discoloration when compared to a control tone based on conditional parameters.

In some embodiments of the system the dermal images may comprise digital photographic color images, for example as captured by a smartphone camera. In some alternative embodiments the dermal images may comprise thermal images, for example as captured by an infrared camera. In other alternative embodiments the dermal images may comprise both photographic visible color and infrared images, for example as captured by a smartphone camera having digital sensors for photographing red, green, blue and infrared wavelengths. In some alternative embodiments the dermal images may comprise ultraviolet images, for example as captured by an attachment to a smart device for using ultraviolet light exposure and/or ultraviolet lens filtering. In some embodiments of the system, the dermal images may be calibrated and/or corrected by applying a virtual tristimulus colorimeter to adjust for hue, saturation or lightness differences resulting from variations in the photographic environment and/or the camera equipment. In some embodiments such a virtual tristimulus colorimeter may be implemented, in part, as a smartphone application.

In some embodiments identification of one or more dermal image control tones may be performed to establish a control tone. Establishing such a control tone, may also comprise determining one or more Fitzpatrick skin type parameters. In some embodiments various quantifications may then be performed to determine the severity of tone discoloration when compared to an established control tone. One or more of a variety of metrics may be employed, in some embodiments, to compute color distances and/or weighted color distances thereby quantifying dermatological differences of interest, for example redness, heat, pigmentation, jaundice, etc.

In some embodiments facial images may also be augmented with color-coded graphics to reflect Ayurvedic and/or Chinese medicine interpretations, and to overlay relevant information onto the facial images to report such information.

Some embodiments of the PBVCES's knowledge base perpetually refine and optimize their predictive logic through equating data and pattern discovery. This may be driven by proprietary inference, ontology and persuasion engines which allow the PBVCES to learn and report new insights within structured reports for professionals from a variety of disciplines.

FIG. 1 illustrates one embodiment of a PBVCES platform 100. As illustrated in FIG. 1, embodiments of a PBVCES platform 100 may be architected to include one or more of the following components: Connected device(s) for dermal image data capture; Compute platform jobs 49 for assessment data, ontology archiving, deductive inferencing processes, abductive inferencing processes, allusive persuasive processes, Business to Consumer (B2C) data reporting, and implementation scoring; Display visualization platform(s) 13 for dermal images data capture, assessment, markers generation, asymmetrical and atypical measurement processes; Business-to-Business (B2B) portals 101-102 and applications for professionals and experts; B2C portal(s) 103 and applications for consumers and clients; Back-end Application Programming Interfaces (APIs) for registered users login and access rights management; B2C and B2B data deporting; Operational data repositories; Data warehouse, data marts, knowledgebase and databases of facts, data lakes 23; and/or Enterprise back-end and eCommerce systems.

Figure 2:
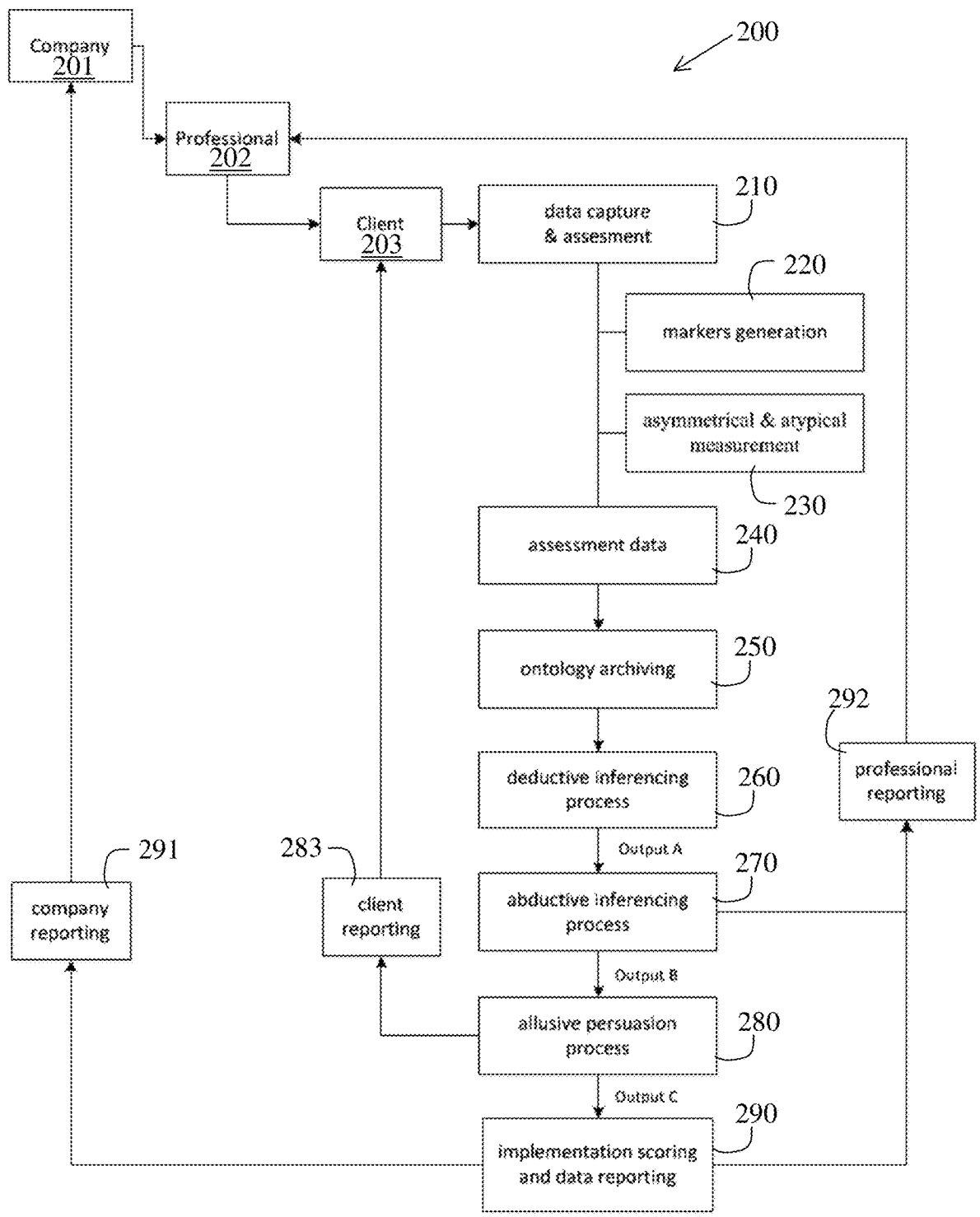
FIG. 2 illustrates a high level flowchart of one embodiment of proprietary PBVCES processes.

FIG. 2 illustrates a high level flowchart of one embodiment of proprietary PBVCES processes 200. The high level flowchart for such an embodiment may comprise the following processes: image data capture and assessment 210; markers generation 220; asymmetric and atypical measurement 230; assessment data 240; ontology archiving 250 of assessment data 240; deductive inferencing process 260; abductive inferencing process 270; professional reporting 292 to professionals 202; allusive persuasion process 280; client reporting 283 to clients 203; implementation scoring 290; and company data reporting 291 to companies 201.

It will be appreciated that PBVCES processes may evolve and/or be adjusted over time. Some example embodiments of these processes are illustrated below.

Figure 3:
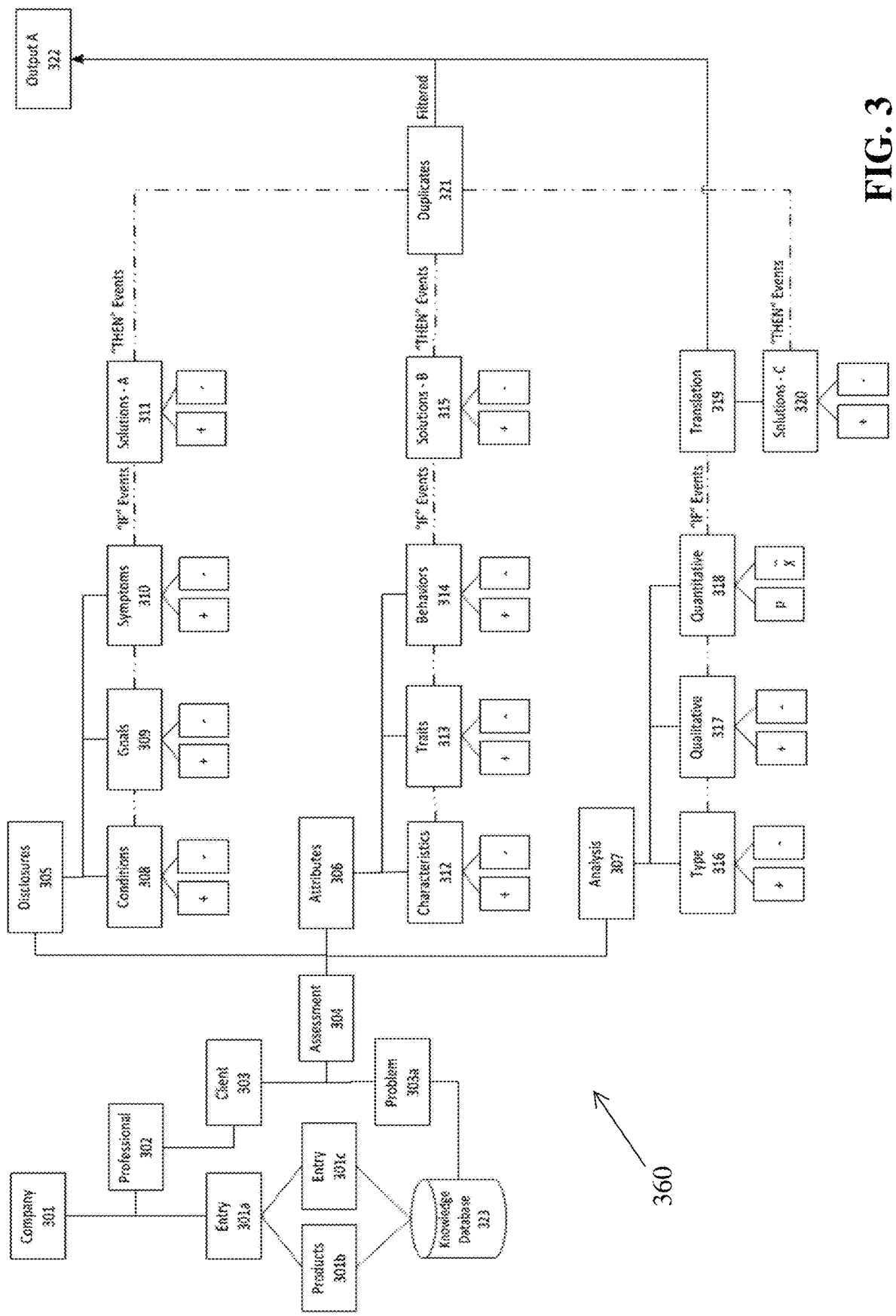
FIG. 3 illustrates, according to one embodiment of the proprietary PBVCES processes, an ontology archiving of assessment data and deductive inferencing process.

FIG. 3 illustrates, according to one embodiment of the proprietary PBVCES processes, an ontology archiving of assessment data and deductive inferencing process 360. In certain embodiments, PBVCES process 360 may correspond to ontology archiving 250 of assessment data 240 and deductive inferencing process 260.

In embodiments of PBVCES process 360, company 301 may comprise a producer of products or services distributed by professionals 302. For example, the PBVCES platform system and applications may be marketed to companies 301 that produce professional products 301b and services entries 301a and 301c. The PBVCES platform may customize an application for professionals 302 distributing their products 301b and services entries 301a and 301c. Thus products 301b may be an inventoried set of items solicited by a professional 302. The services entries 301a and 301c may be a set of expert actions solicited by a professional 302. Professional 302 may comprise an educator, consultant or specialist supplying advice, products and services. Embodiments of the PBVCES platform may track, for example, how the client 301 implements protocols through surveyed interactions and converted clicks of the persuasive information. Embodiments of the PBVCES platform could provide data back to company 301 and professional 302 separately, e.g. through their respective portals.

Client 303 may comprise an individual seeking professional support for a problem 303a. Entry 301a may comprise a submitted company 301 solution to a given problem 303a. The PBVCES platform could provide a template to add entries of products 301b, and services entries 301a and 301c, i.e. solutions that they may offer which can be stored in the platform database of facts. This information may then be correlated to disclosures 305, attributes 306 and analysis 307 outcomes, i.e. problems 303a. Thus assessment 304 may comprise the identification of products 301b and services entries 301a and 301c applicable to problems 303a through the collective result of disclosure 305, attributes 306 and analysis 307.

Disclosures 305 may comprise symptoms, goals and/or conditions indicated by client 303. Attribute 306 may comprise a professionally observed characteristic, trait or behavior of the client 303. Analysis 307 may comprise qualitative 317 and quantitative 318 data from comparable third-party hardware or software. Knowledge database 323 may comprise the inference of source information. Database entries may be programmed into the PBES platform as a series of "IFs" and "THENs" events. As the professionals 302 access the application promoted by the company 301, the entered products 301b, the services entries 301a and 301c, the solutions 311, 315 and 320 may be reported, e.g. as "THENs" to the disclosures 305, attributes 306 and measurable analysis 307 as "IFs" defined as problems 303a. Duplicates 321 may comprise repeated output of products 301b and services entries 301a and 301c. Duplication may comprise a filtering technique to isolate duplicated "THEN" events. The duplicated events may comprise reported outputs, defined as output A 322. Conceptually, the more products 301b and services entries 301a and 301c get duplicated, the more relevant it may be in supporting the problem. All unduplicated outputs may then be cancelled and/or not reported in some embodiments.

In one embodiment the PBVCES is a computer platform that enhances the decision-making ability of a human expert, e.g. through artificial intelligence, by offering predictive logic services resulting from the collection, processing and assorting of qualitative and quantitative data captured from multiple interconnected source inputs. The platform knowledge base may continuously refine and optimize its predictive logic through equating data and pattern discovery. Driven by a proprietary inference engine and related systems, the platform may continuously learn and report new insights within structured reports that can be developed for professionals and registered users from a variety of disciplines.

Figure 4:
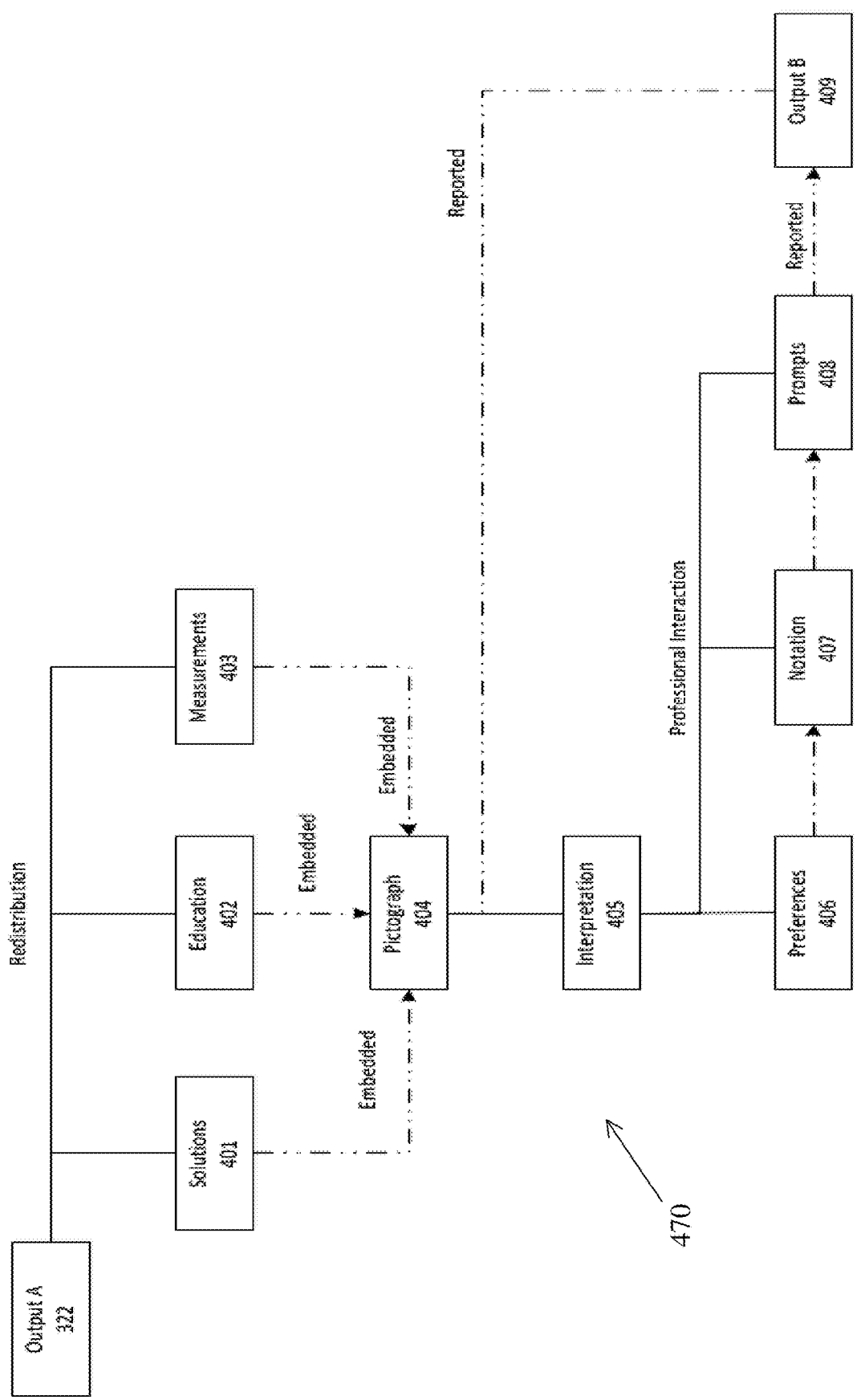
FIG. 4 illustrates, according to one embodiment of the proprietary PBVCES processes, an abductive inferencing process and professional reporting.

FIG. 4 illustrates, according to one embodiment of the proprietary PBVCES processes, an abductive inferencing process and professional reporting 470. The abductive inferencing process may comprise redistributing the duplicated events, i.e. output A 322, from the ontology archiving of assessment data and the deductive inferencing process to the solutions 401, education 402 and measurements 403 processes. Solution 401 may comprise an advised proposal of a professional 302 to support a client 303 based on a circumstantial problem 303a as the reason that client 303 is seeking professional 302 support. Measurement 403 may comprise a unique automated translation of data entry. The measurement 403 input may comprise a relationship of an automated proprietary translation of an "IF" event (analysis data) with "THEN" events from a particular set of company 301 products and services.

Pictograph 404 may comprise a reported graphical representation of a filtered output. In some embodiments, the PBVCES platform may also comprise embedding filtered "THEN" events within an interactive pictograph 404 with its uniquely translated measurements 403. The pictograph 404 may comprise a hub of engagement between the professional 302 and client 303. The pictograph 404 may also comprise offering added education 402 for exploration beyond reported data. The interpretation 405 may comprise a professional 302 interaction with a pictograph 404. In some embodiments, professional 302 may provide their interpretation 405 of the translated measurements 403 and "THEN" events through a guided interaction of preferences 406, notations 407 and prompts 408 which may be added into the pictograph 404 dataset. Preference 406 may also comprise a guided process of setting the client 303 protocol reminders. Notation 407 is a free text note added professionally to a pictograph 404. Prompt 408 may also allow professional 302 to emphasize or prioritize reported data. In some embodiments, the outcome of the abductive inferencing process 470 may comprise a set of prompts 408 that may define the professional reporting output B 409 to the allusive persuasive process and client reporting.

Figure 5:
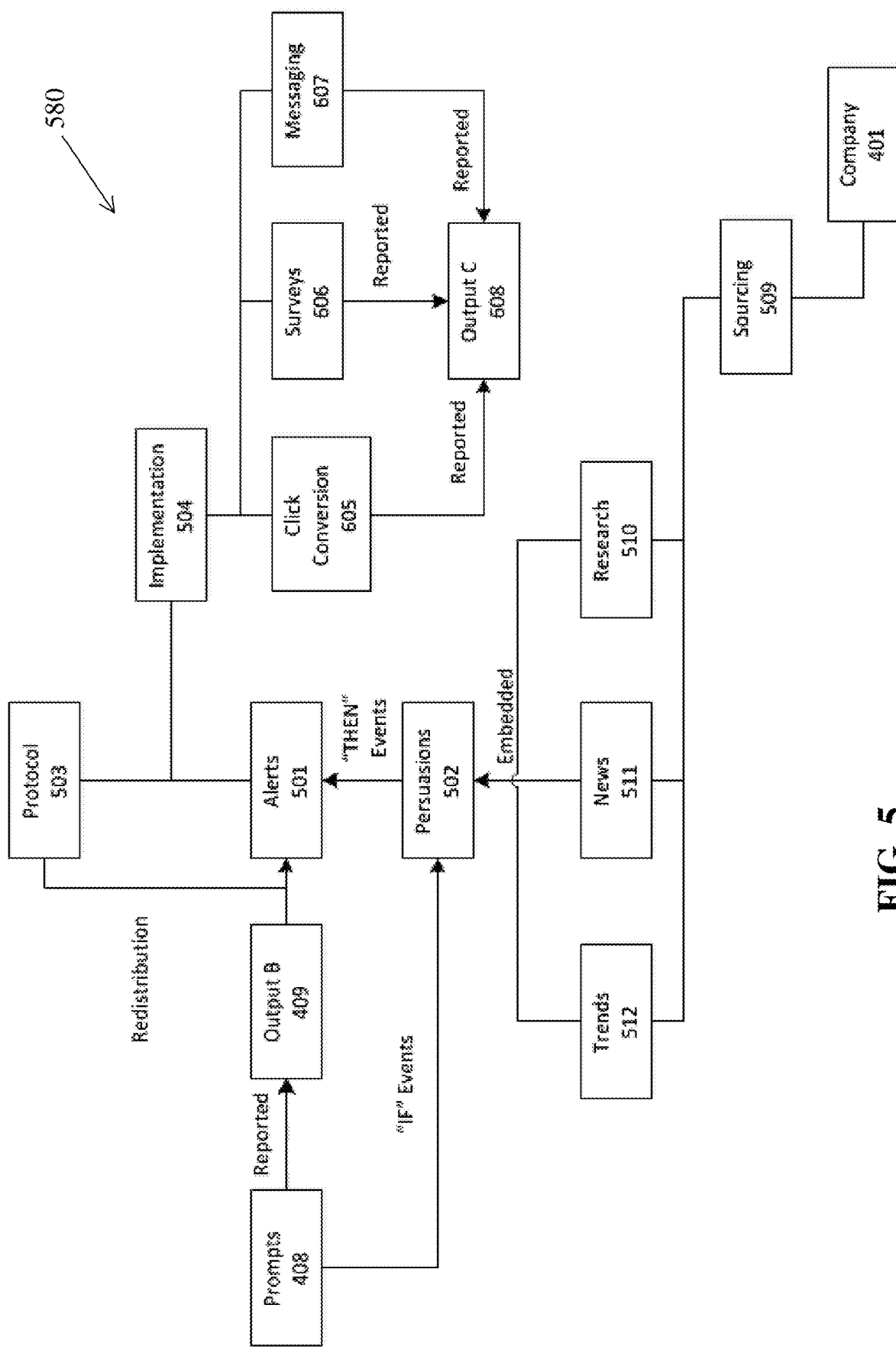
FIG. 5 illustrates, according to one embodiment of the proprietary PBVCES processes, an allusive persuasion process and client reporting.

FIG. 5 illustrates, according to one embodiment of the proprietary PBVCES processes, an allusive persuasion process and client reporting 580. The allusive persuasion process and client reporting 580 may comprise redistributing reported prompts 408 and output B 409 from the abductive inferencing professional reporting to the protocol 503, alerts 501 and persuasions 502 processes. Protocol 503 may comprise a recommended set of action for the client 303 based on alerts 501 generated as push notices that motivate the client 303 actions regarding the generated prompts 503. Persuasion 502 may comprise a segment of sourcing 509 of information which is added to the alerts 501. The PBVCES platform may add a persuasion 502 to alerts 501 when a client 303 is asked to prompt follow-through 602 with a recommendation. Through tips and education such as trends 512, news 511 and research 510 about particular products 301b and services entries 301a and 301c from company 301, the client 303 may be allusively conditioned to be proactive in implementing protocol 503. Implementation 504 may comprise the proficiency of a client 303 to follow through on a protocol 503. The PBVCES platform may track the protocol 503 progress through surveys 606 interaction and click conversion 605 of the persuasion 502 information provided by companies 301.

Figure 6:
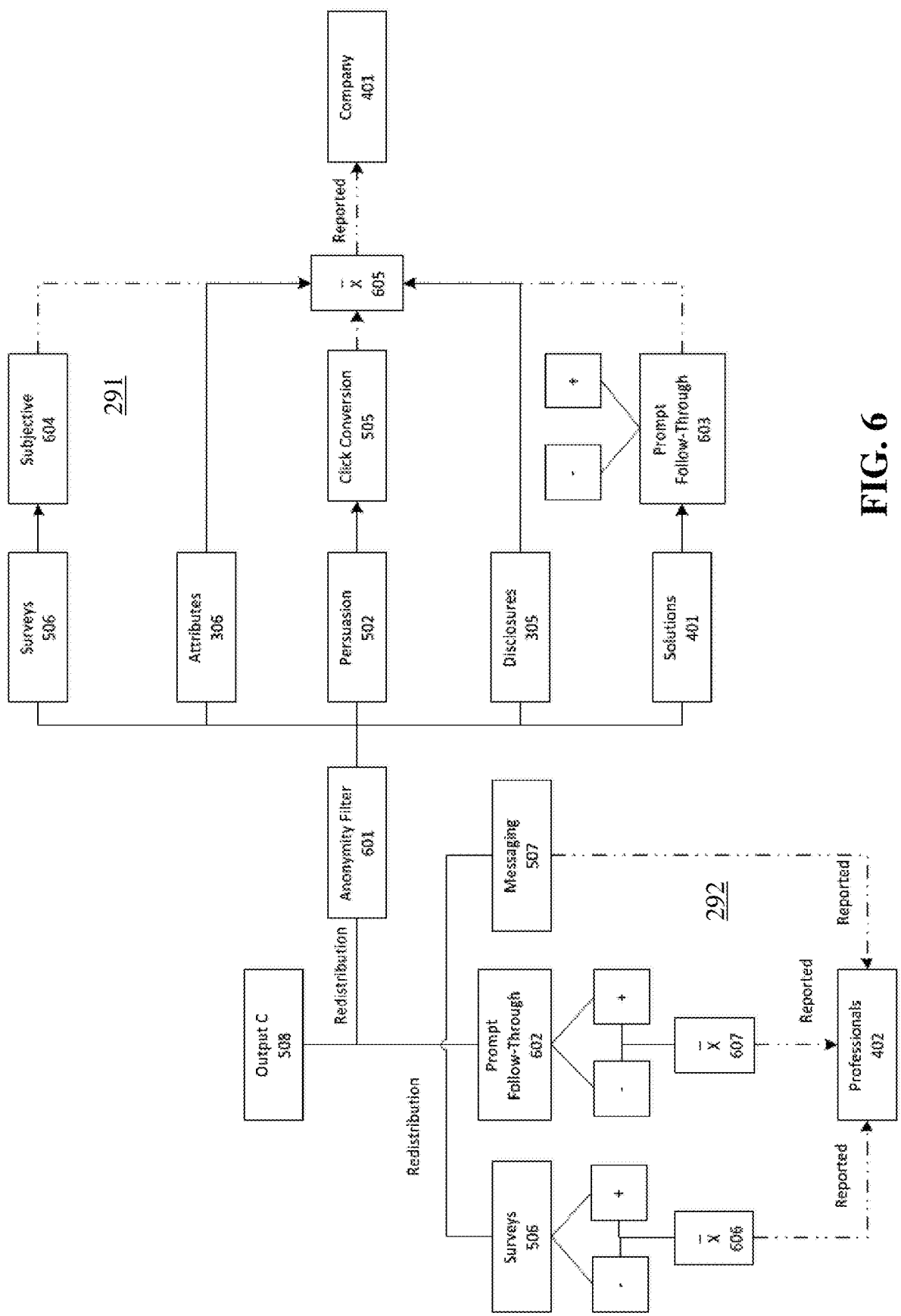
FIG. 6 illustrates, according to one embodiment of the proprietary PBVCES processes, implementation scoring and data reporting.

FIG. 6 illustrates, according to one embodiment of the proprietary PBVCES processes, implementation scoring and data reporting 291 and 292. The implementation scoring and data reporting 291 and 292 represent information shared by the PBVCES platform to the company 301 and professionals 302 resulting from an implementation 504 of the proficiency of a client 303 to follow through a protocol 503. This information may be fed back to the company 301 and professionals 302 separately through their respective B2B portals. The company 301 may get an implementation scoring and data reporting 291 from anonymity filtered 601 client 303 and based on the individual scoring of surveys 506, attributes 306, persuasion 502, disclosures 305 and solutions 401. In some embodiments the scoring for surveys 506 may be adjusted based on a subjective 604 filtering. The scoring for persuasion 502 may also be adjusted based on click conversion 505, and scoring for solutions 401 may be adjusted based on prompt follow-through 603. On the other hand, the scoring for attributes 306 and scoring for disclosures 305 may be unfiltered.

Professionals 302 may get an implementation scoring and data reporting 292 from the surveys 506, prompt follow-through 602 and messaging 507, which e.g. may be weighted 606 and 607 and then reported to professionals 302 in some embodiments.

Figure 7A:
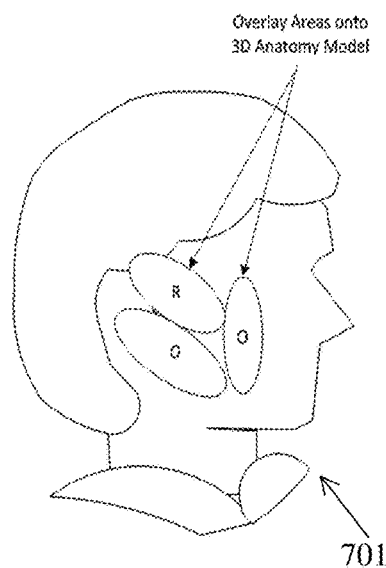
FIGS. 7A, 7B and 7C illustrate several examples of markers generation according to embodiments of the proprietary PBVCES processes.
Figure 7B:
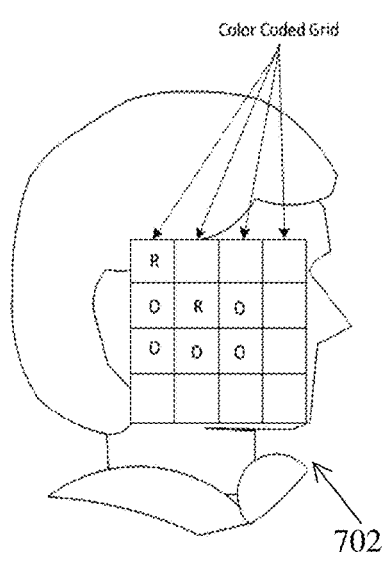
Figure 7C:
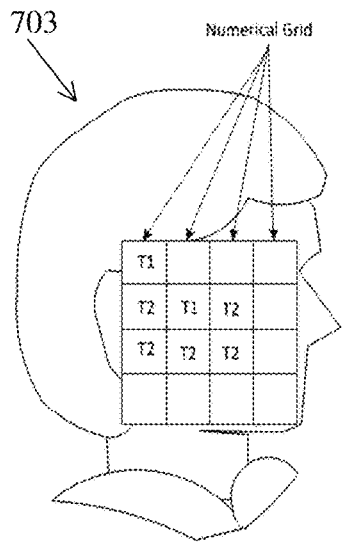

FIGS. 7A, 7B and 7C illustrate several examples of markers generation 701-703 according to embodiments of the proprietary PBVCES processes. To highlight areas of concern following the capture of dermal images, there may be types of markers that the professional and client can select and toggle to review results from a dermal image assessment. Three examples of such marker types are illustrated.

One marker type may be considered as a glowing graphics effect of those parts of the human anatomy that signify the relevance of regions with atypical results. For example, setting color markers to red, orange and blue may indicate clear variation of regions with atypical results. FIG. 7A illustrates a glowing graphics effect 701 of a part of the human anatomy. In this example, red, listed as R, may be used to define an inflammation or irritation of regions, e.g. in which temperatures and/or redness are significantly increased. Similarly, orange, listed as O, may be used to define less sensitive or irritated regions, e.g. in which minor increases of temperature and/or redness are identified. Blue may be used to define an inactive, congested or restrictive regions whereby temperature and/or redness differentiations are significantly reduced.

Another marker type may be based on color coded grids of the 3D model to signify significant differences. In some embodiments, the grid areas of average dermal image tones may be left transparent in order to highlight the key areas of interest. FIG. 7B illustrates one such embodiment of a grid based area 702 on a 3D human anatomy model. Using the same marker colors example as before, grid areas of significant increased temperatures and/or redness are identified as red, listed as R. Similarly, the grid areas of minor increased temperatures and/or redness are identified as orange, listed as O. Finally, the grid areas of significant decreased temperatures and/or redness are identified as blue.

FIG. 7C illustrates a numerical type of marker grid 703 and provides e.g. the collected temperatures and/or redness values averaged for each grid 703 area in the 3D human anatomy model.

It will also be appreciated that embodiments of the proprietary PBVCES processes may be used in conjunction with and in accordance with Ayurvedic medicine and/or Chinese medicine. Ayurvedic medicine (also called Ayurveda) is one of the world's oldest medical systems, originating in India more than 3,000 years ago Like the medicine of classical antiquity, Ayurveda has historically divided bodily substances into five classical elements: earth, water, fire, air and ether.

Chinese medicine is a style of traditional medicine built on a foundation of more than 2,500 years of Chinese medical practice. One theory, called Wu Xing, also considers five elements: wood, fire, earth, metal and water. These five elements may be respectively associated with five colors: green, red, yellow, white and black. Similarly, five organs, the liver, the heart, the spleen, the lungs and the kidneys are called the yin organs; and another five organs, the gall bladder, the small intestine, the stomach, the large intestine and the urinary bladder are called the yang organs.

In Chinese medicine, Wu Xing is a valuable tool for helping to understand normal physiology. For example, it can be used to explain the process of aging, how the various tissues and organs support each other, and the chains of command and control within the body in order to maintain balance. With a rudimentary knowledge of constructive and/or destructive five-phase cycles of Wu Xing, one can be creative in finding personalized cures by weakening that which is too strong and strengthening that which is too weak.

Zang-fu is a Wu Xing cycle of five zang organs, six fu organs, and their functions. The Zang-fu is a collection of organs that produce and regulate qi within the body. The zang organs refer to the five organs that are yin. Collectively, their primary purpose is to produce and store qi, xue (blood), Jinye (body fluids), Jing (essence), and shen (spirit). They are the five yin organs of Wu Xing: the liver, the heart, the spleen, the lungs, and the kidneys. The fu organs refer to six organs that are yang. Collectively, their primary function is to transmit and digest nutrients without storing them and to excrete waste. They are the yang organs of Wu Xing plus one more organ, which does not have a Western anatomical equivalent, i.e.: the gall bladder, the small intestine, the stomach, the large intestine, the urinary bladder and the sanjiao. The sanjiao can be thought of as three placeholders, cavities or jiao for the organs within the body's trunk: the upper jiao to hold the heart and lung, the middle jiao to hold the spleen and stomach; and the lower jiao to hold the kidney and urinary bladder.

Mien Shiang, literally translated as 'face reading', is otherwise known as physiognomy. One can determine anyone's Wu Xing—five element personality type—their character, behavior, and health potential—by analyzing their face. Some forms of face mapping are rapidly taking center stage at spas and clinics, and combine ancient Chinese medicine and clinical dermatological procedures. Thus it may be appreciated that embodiments of the proprietary PBVCES processes herein disclosed may be easily adapted for use in conjunction with and in accordance with such techniques.

Every part of the face reveals something significant. There are five to ten unique face shapes, the two sides of the face, three primary zones, and twelve principal features including: ears, hairline, forehead, brow bones, eyebrows, eyes, cheeks, nose, lips/mouth, chin and jaw. By studying skin conditions and changes, one can determine inner imbalances and stressed areas of the body. Because each area of the face is said to relate to an internal body area, disharmony in that internal area will, in turn, lead to a change in the complexion, texture or moisture of the corresponding facial area. For example, red, pustular breakouts may be indicative of yang-type energy, and oily, comedone-prone breakouts may be indicative of yin-type energy. Lines may indicate a long-term imbalance or stress, while breakouts may indicate a more short-term imbalance or stress.

It will be appreciated, therefore, that in some embodiments facial images may be augmented with color-coded graphics to reflect such Ayurvedic and/or Chinese medicine interpretations, and to overlay relevant information onto the facial images to report such information.

FIGS. 8A, 8B, 8C, 8D, 8E and 8F illustrate one embodiment of a process 800 for asymmetrical and atypical measurements. As illustrated in FIG. 8A, a professional registered user, in one embodiment of a B2B application, may select the area of the body, represented as a 3D surface area 810, for which the dermal images are to be collected. In this example, the application 805 may illustrate angles and distances of the dermal images to be taken by a thermal imager accessory, for example a connected smartphone infrared camera. As illustrated in FIGS. 8B and 8C, when the thermal images get captured, the professional may be prompted by the B2B application to identify the key points (e.g. K1-K7) within the captured thermal image that designate the area parameters of temperatures to be considered. In FIG. 8D, once the key points are identified, the measured temperatures (e.g. T1, T2, etc.) may be overlaid onto the 3D model 815, for example, using the designated key points per image.

As illustrated in FIG. 8E, the parts and layers of the 3D model 815 may use correlating grids in some embodiments. Each square of the grid may comprise an average of corresponding temperatures, listed as CT1 in FIG. 8E, based on the key point overlays. Selected groups of squares may also have corresponding data relating to internal anatomy and other types of education per region. In FIG. 8F, once all image temperatures (or redness values, pigmentation, etc.) have been added to the 3D model 815, asymmetrical and range measurements can be generated. Markers may then be used to highlight areas of atypical measurements.

It will be appreciated that professional registered user may be provided the ability to increase or to decrease temperature (redness value, and/or dark pigmentation) ranges for example, as a parameter for highlighting consideration. In some embodiments this feature could provide a means to intensify increased points of concern or minimally isolate areas of concern—offering flexibility based on the particular professional's requirements.

In some embodiments an atypical tone expert system may comprise a computer system that enhances the decision-making ability of a human expert through artificial intelligence. For example, it may function by collecting, processing and assorting dermal images with qualitative and quantitative data through an interlinked network of source inputs.

Figure 9:
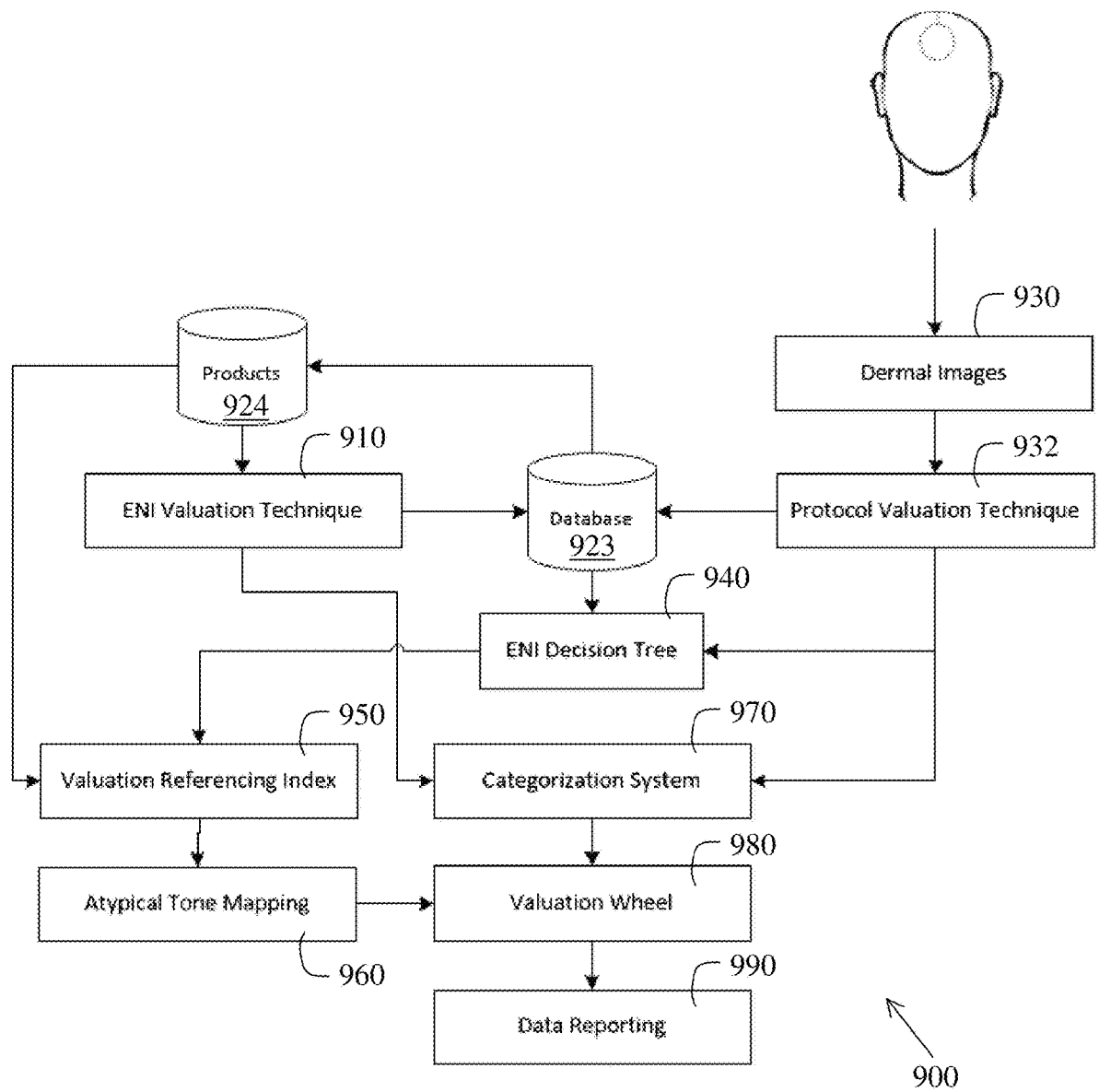
FIG. 9 illustrates, according to one embodiment of the proprietary PBVCES processes, the main components of an atypical tone expert system.

FIG. 9 illustrates, according to one embodiment of the proprietary PBVCES processes, the main components of an atypical tone expert system 900. As illustrated in FIG. 9, the atypical tones expert system 900 may comprise the following individual sub-systems, as listed thereof: ENI valuation technique 910 and ENI decision tree 940; products and system expert database 923-924; dermal images 930 and protocol valuation technique 932; valuation referencing index 950; atypical tone mapping 960; and valuation wheel 980 and reported data 990. In some embodiments, dermal images 930 may be processed in accordance with one or more protocol valuation technique 932 and recorded in a database 923, along with and/or associated with results from one or more ENI valuation techniques 910 having products 924 as inputs, in order to provide valuation data to the ENI decision tree 940 and categorization system 970. Example embodiments of the components of an atypical tone expert system 900 are described below, in greater detail.

Figure 10:
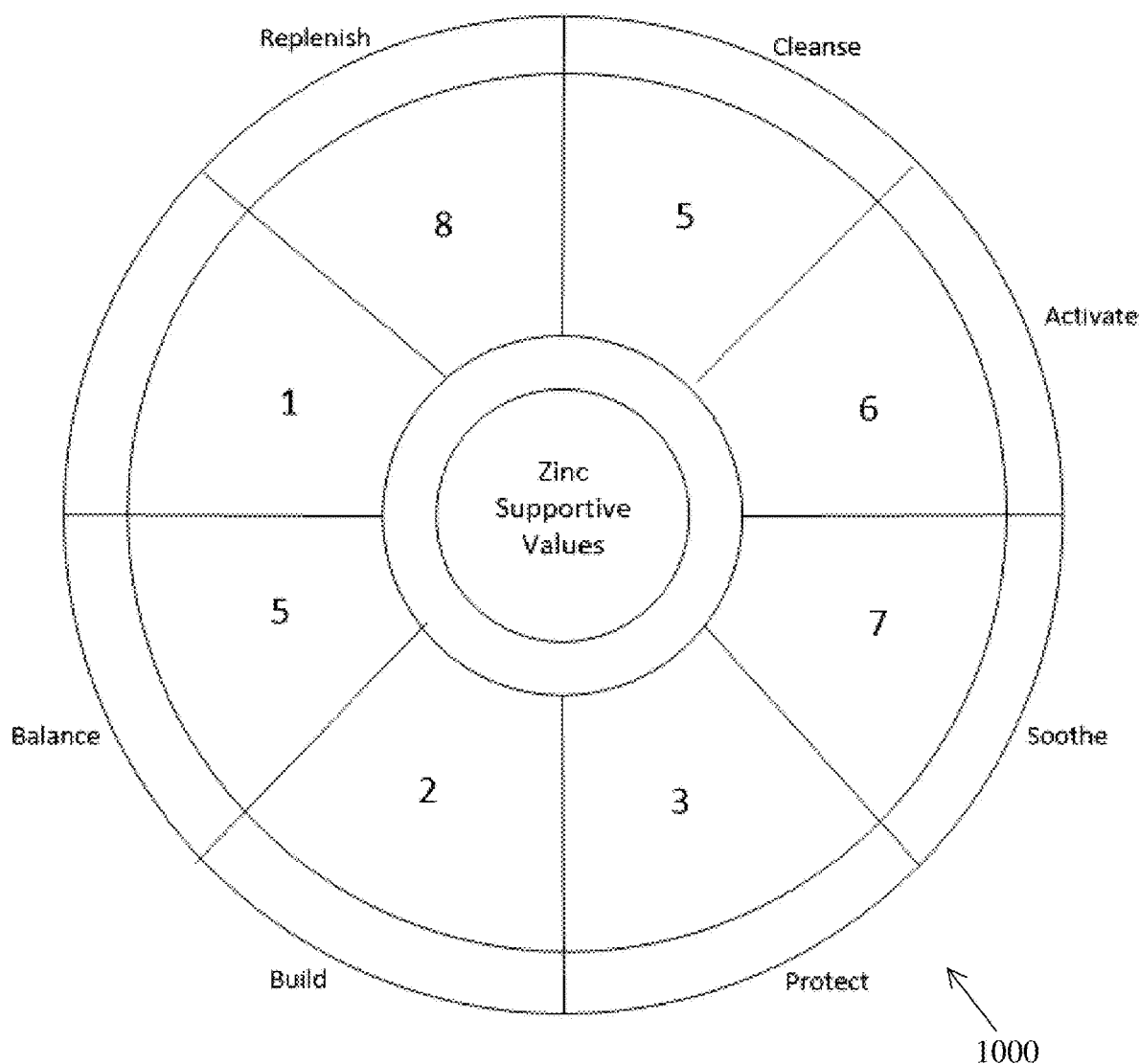
FIG. 10 illustrates, according to one embodiment of the PBVCES, an example of element, nutrient or ingredient (ENI) valuation.

FIG. 10 illustrates, according to one embodiment of the PBVCES, an example of element, nutrient or ingredient (ENI) valuation 1000. Some embodiments of ENI valuation 1000 technique may comprise one or more methods for assigning values to elements, nutrients and ingredients based on certain supportive properties and functions. An element, nutrient or ingredient found within foods, supplements, medications or skincare products may have multiple supportive functions and properties. These functions and/or properties may then in turn, aid, affect or influence the mind and body while attempting to address a health, wellness or skin condition, concern or goal.

In some embodiments, those functions and/or properties may be classified within eight key supportive categories, for example illustrated as: soothe, protect, build, balance, activate, cleanse, replenish and nourish. For example. soothe may comprise a property and/or be representative of a function to calm, relieve or reduce. Protect may comprise a property and/or be representative of a function to guard, insulate or shield. Build may comprise a property and/or be representative of a function to strengthen, improve or develop. Balance may comprise a property and/or be representative of a function to stabilize, control or regulate. Activate may comprise a property and/or be representative of a function to move, circulate or stimulate. Cleanse may comprise a property and/or be representative of a function to eliminate, sanitize or exfoliate. Replenish may comprise a property and/or be representative of a function to refill, moisturize or hydrate. Nourish may comprise a property and/or be representative of a function to feed, sustain or preserve.

For example, ENI valuation 1000 illustrates the technique as applied to the mineral zinc. According to the ways in which zinc functions within the body as well as how it is utilized to support wellness and skincare goals, it may become apparent that it can fall into multiple categories. Zinc is needed for the normal development of certain cells within the body. These functions can be labeled as nourishing and building. Zinc also acts as an antioxidant and stabilizes membranes—a protecting function. Zinc can directly fight against bacteria and be used as a supportive agent in removing infections. This may be seen as a cleansing function. Thus as functions and/or properties of zinc are listed, it may become apparent that the replenishing and soothing properties of zinc are minimal.

As such, one ENI valuation 1000 for zinc may be expressed as an ordered listing of supportive values, as follows: 1, nourish; 2, build; 3, protect; 4, cleanse; 5, balance; 6, activate; 7, soothe; and 8, replenish. The order of ENI values may vary based on wellness or appearance conditions, concerns or goals. As these ordering variations are researched for different elements, nutrients and ingredients, it may become apparent that a reordering may be chosen, based on whether the element, nutrient or ingredient was being utilized in a) acute and critical circumstance, b) general care and maintenance circumstance or c) chronic and prolonged circumstances. Therefore, the ENI valuation 1000 technique may provide three versions for each element, nutrient or ingredient being scored, as follows: Acute and Critical Score, defined as ENI-ACS; Care and Maintenance Score, defined as ENI-CMS; and Chronic and Prolonged Score, defined as ENI-CPS. Furthermore, embodiments of a wheel with the eight key supportive categories is designed to quickly reference the ordering of support of any element, nutrient or ingredient.

It will be appreciated that integration of an atypical tone expert system can allow for identification, classification and measurement of discoloration tones outside the spectrum of standardized normal tones. Data from the system can be used to prioritize key supportive actions that could help in addressing specific issues. Thus the PBVCES provides a mechanism for optimizing predictive logic of products and services considered most relevant and supportive in addressing conditions by a systematic process of classifying discolorations and calculating their severities. Professional registered user may be provided with the ability to increase or to decrease temperature, redness value, and/or dark pigmentation ranges as parameters for highlighting consideration. In some embodiments such features could provide a means to intensify points of concern or minimally isolate areas of concern, with flexibility based on those professional's preferences.

Figure 11:
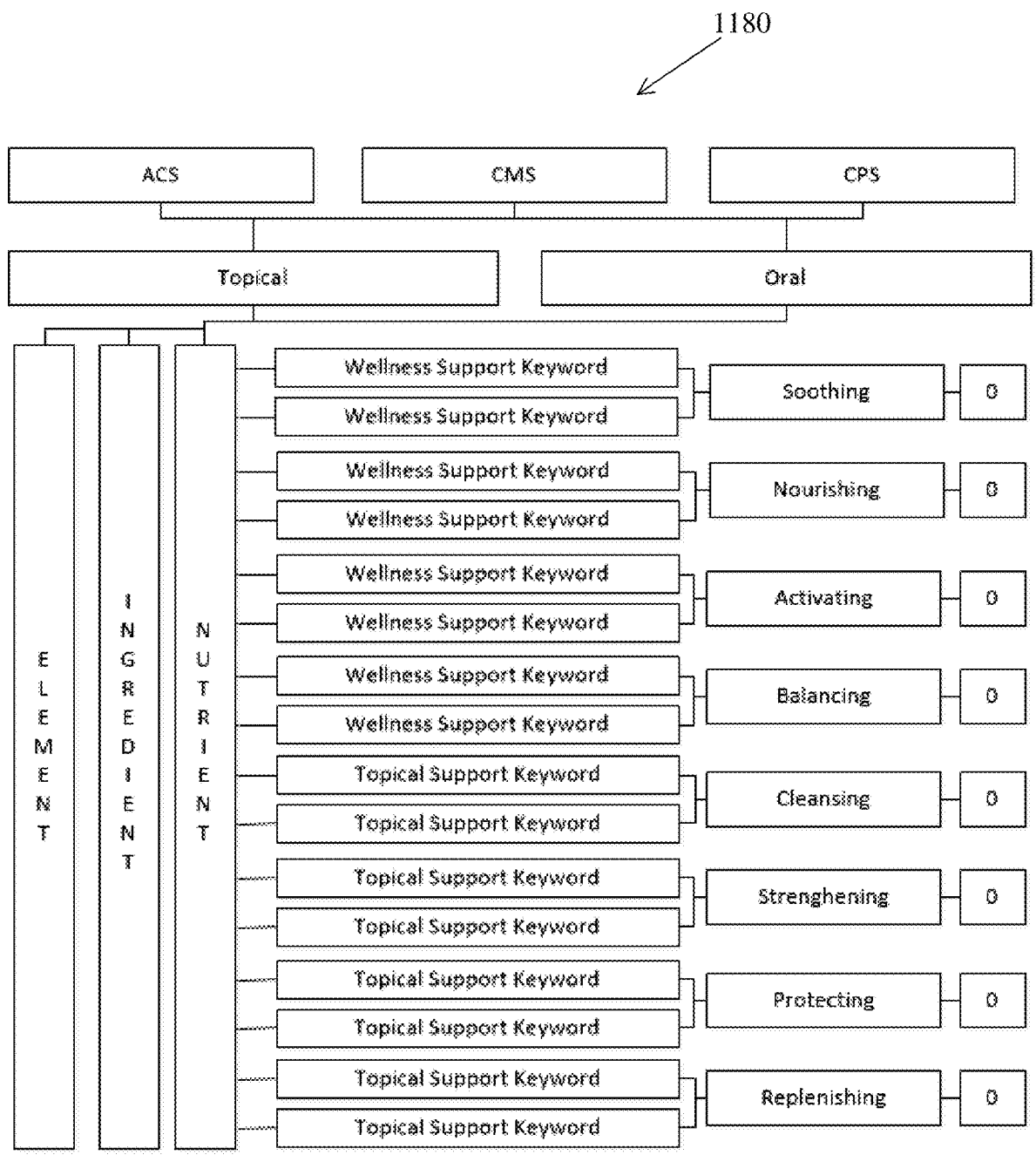
FIG. 11 illustrates, according to one embodiment of the PBVCES, a template for the ENI valuation.

FIG. 11 illustrates, according to one embodiment of the PBVCES, a template for the ENI valuation 1180. As functions and/or properties of an element, nutrient or ingredient are classified within the eight categories exemplified by ENI valuation 1000, a weighted distribution may become apparent. This process may allow for the development of a classification system to calculate weighted values of elements, nutrients or ingredients through the ordering of supportive functions and properties into categories. Such a system may be referred to in some embodiments as an ENI valuation 1180 technique.

Upon identifying the element, nutrient or ingredient, it may be classified as being topical and/or oral support. In one embodiment the next step may be to enter eight key words pertaining to functions and properties to be entered within topical, acute and critical circumstances as well as for general care and maintenance circumstances. Each supportive keyword or phrase may be manually linked to one or more key supportive categories. When a category is linked, it may also be given a point, for scoring purposes. After entering keywords or phrases and linking them to categories, the points may be tallied for each category. The categories may then be sequentially listed 1 through 8 from the highest scoring to the lowest scoring, 1 being the highest scoring and 8 being the lowest scoring. The higher the score, the greater the priority of support. Oral and topical products that have a number of combined elements, nutrients and or ingredients may also be classified using the ENI valuation 1180 technique by adding the sum total ENI values of the elements, nutrients and or ingredients within the product and then averaging to determine the products ordered value of supportive properties.

Figure 12:
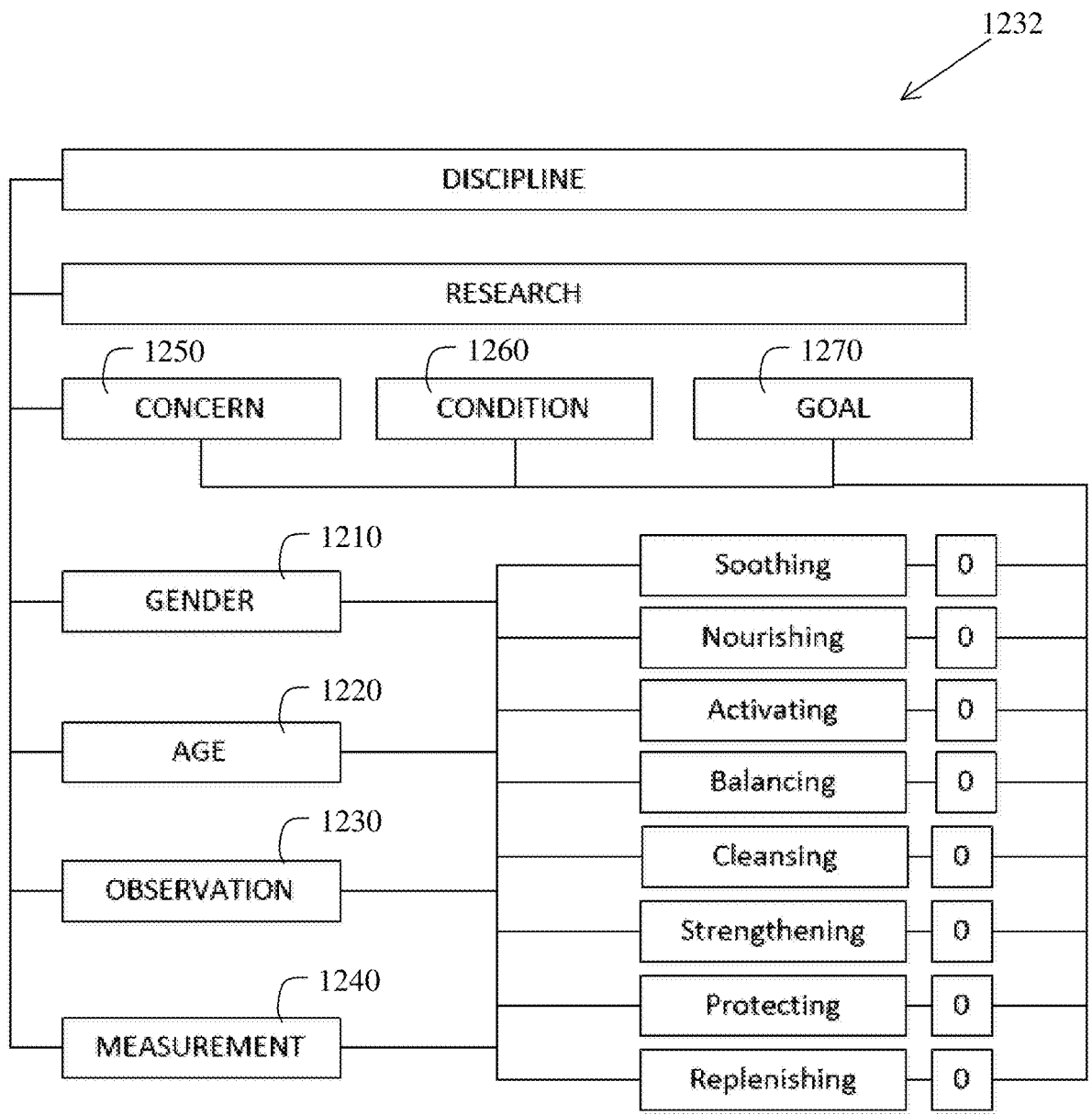
FIG. 12 illustrates a method for protocol valuation according to one embodiment of the PBVCES.

FIG. 12 illustrates a method for protocol valuation 1232 according to one embodiment of the PBVCES. Embodiments of the protocol valuation 1232 technique may comprise a method for creating a set of measurable values for health, wellness and skincare protocols expressed by a condition, concern or goal. Any health, wellness or skin condition, concern or goal requires multiple supportive actions to thoroughly and comprehensively address the issue and reach optimal results. Similar to the ENI valuation 1180 technique, those supportive actions may be classified within the same eight key supportive categories: soothe, protect, build, balance, activate, cleanse, replenish and nourish. Based on measurable parameters relating to conditions, concerns or goals, a weighted distribution of the eight supportive categories may be generated with the prioritization of support needed to address an issue. For some embodiments, this method may be performed as illustrated in protocol valuation 1232.

For example, a female patient in her middle thirties may be concerned with a case of severe acne on her jawline. Her goal may be to reduce the acne and prevent future outbreaks. Multiple supportive actions may be required to address the issue and reach optimal results, with elements, nutrients and ingredients identified as supportive options. Under certain circumstances, the main priority may be to cleanse the pores and surface area of potential bacteria. Secondarily, the skin could need to be soothed of irritation and protected from future infection. Based on other measurable parameters, it may be highlighted that there is also a need to balance and nourish properties of the patient's skin. One embodiment of protocol valuation 1232 for acne removal in this instance may result as follows: 1, Cleanse to eliminate, sanitize or remove; 2, Soothe to calm, relieve or reduce; 3, Protect to guard, insulate or shield; 4, Balance to stabilize, control or regulate; 5, Nourish to feed, sustain or preserve; 6, Replenish to refill, moisturize or hydrate; 7, Activate to move, circulate or stimulate; and 8, Build to strengthen, improve or develop. An order of protocol values may be derived based on conditional parameters. One embodiment of protocol valuation 1232 technique is designed to calculate these variables to optimize the prioritization process. In some embodiments, these conditional variables may comprise: gender 1210; age 1220; expressed concern, condition or goal 1250-1270; observable concern, condition or goal data 1230; and objective measurable data 1240. Variables may be entered into the system and the eight key support categories may be given points based on linked input parameters, as preprogrammed based on industry research and expert inputs. When all the variables have been entered, the points may be added up in each category. The categories may then be sequentially listed 1 through 8, from the highest scoring to the lowest scoring with 1 being the highest scoring and 8 being the lowest scoring. The higher the score, the greater the priority of support. Furthermore, a wheel with the eight key supportive categories was designed to quickly reference the ordering of support of any treatment plan, supportive protocol or disciplined approach.

Figure 13:
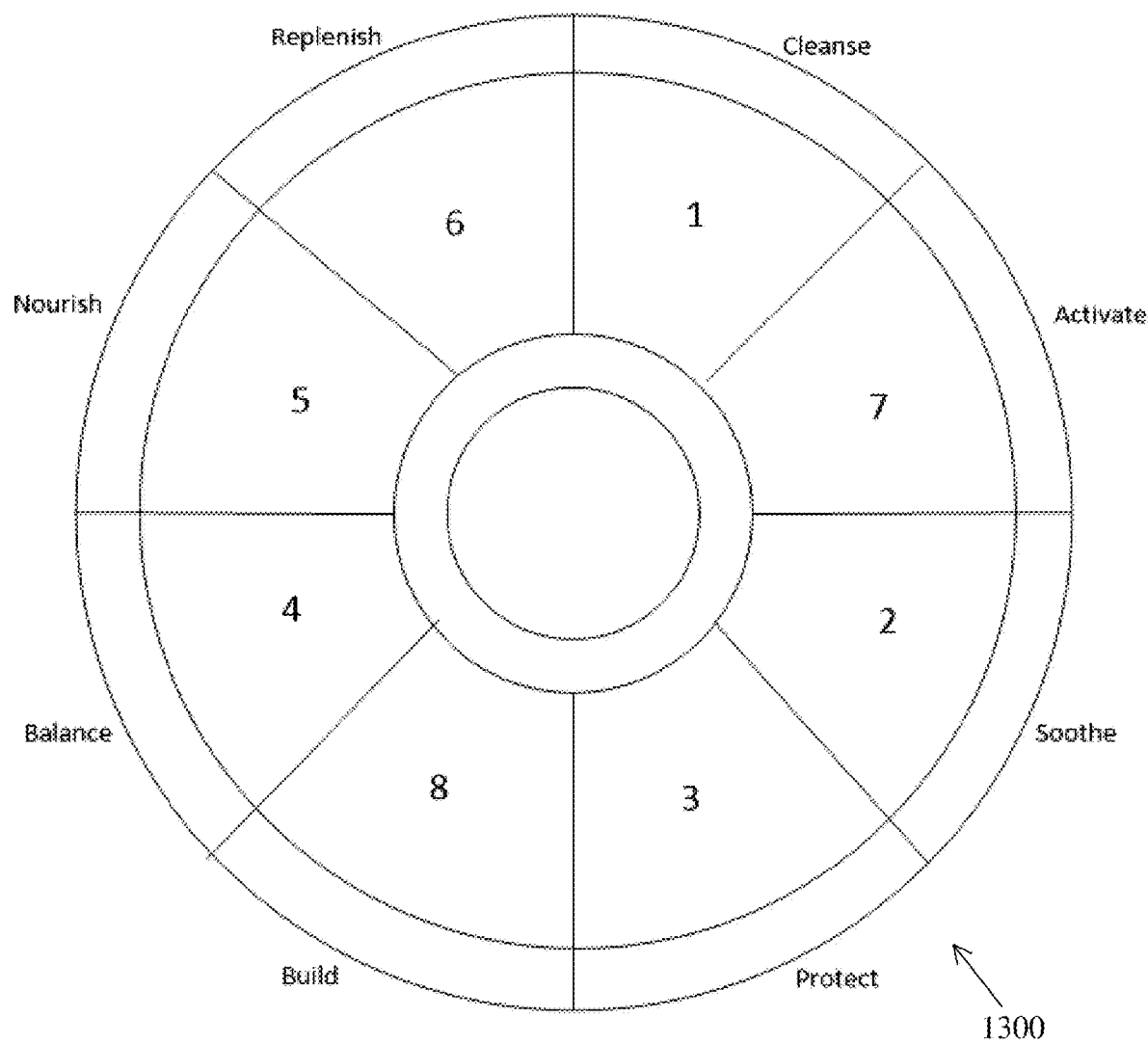
FIG. 13 illustrates, according to one embodiment of the PBVCES, an example of removal protocol valuation.

FIG. 13 illustrates, according to one embodiment of the PBVCES, an example of the acne removal protocol valuation 1300 of the above example. With the understanding that conditions, concerns and goals require multiple supportive actions based on specific parameters and that elements, nutrients and ingredients have multiple supportive properties and functions based on specific parameters, a system that matches ENI valuation sequences with protocol valuation sequences may be developed using the eight key supportive categories. One embodiment of the acne removal protocol valuation 1300 of the above example is illustrated as follows: 1, Cleanse to eliminate, sanitize or remove; 2, Soothe to calm, relieve or reduce; 3, Protect to guard, insulate or shield; 4, Balance to stabilize, control or regulate; 5, Nourish to feed, sustain or preserve; 6, Replenish to refill, moisturize or hydrate; 7, Activate to move, circulate or stimulate; and 8, Build to strengthen, improve or develop. By referencing elements, nutrients and ingredients with supportive properties and functions matching the supportive needs of a condition, concern or goal based on entered parameters, the optimization of treatment plans and protocols can be promptly referenced.

Figure 14:
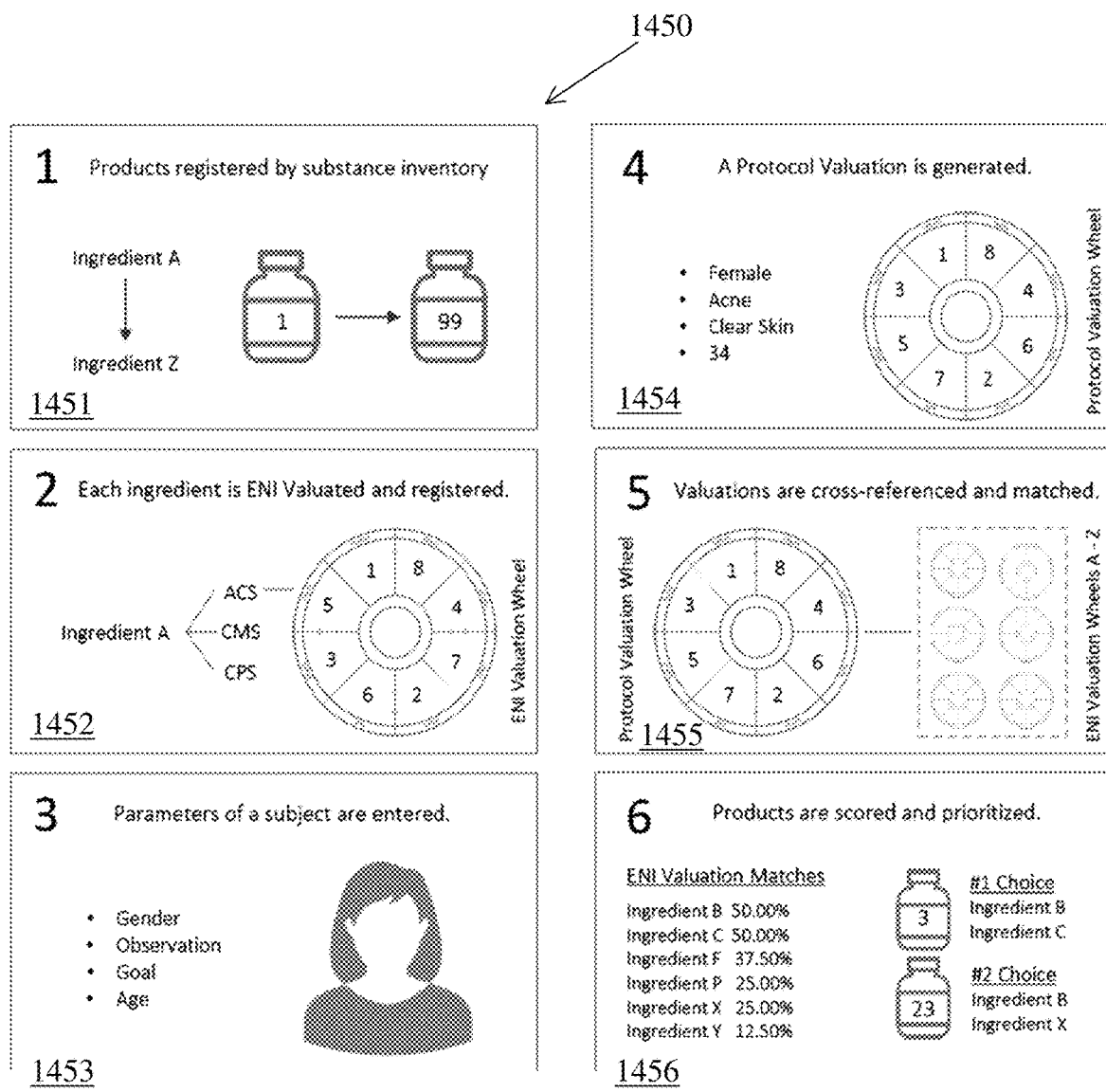
FIG. 14 illustrates, according to one embodiment of the PBVCES, a protocol valuation referencing index.

FIG. 14 illustrates, according to one embodiment of the PBVCES, a protocol valuation referencing index 1450. One embodiment of the valuation referencing index 1450 is a method for matching combined values of elements, nutrients, ingredients to products, medications and foods. The majority of products, foods and medications contain multiple elements, nutrients and or ingredients. Therefore the combined effect of these substances is evaluated for classification purposes by adding the sum total ENI values of the elements, nutrients and or ingredients within the product and then averaging to determine the products ordered value of supportive properties. A first step may be to enter a product, topical or oral, food or medication into the system as well as the associated inventory of elements, nutrients and ingredients of which it is comprised. Those elements, nutrients and ingredients may then be registered through the ENI valuation technique to ensure its complete inventory is measured. Once entered, the system may calculate and classify the product, food or medication based on its support category prioritization. As conditions, concerns or goals are entered along with variables to be considered, a protocol valuation can be generated and cross-compared to the valuation reference index for identifying optimal support.

In one embodiment, a six-step process may be used to generate a protocol valuation referencing index 1450. Step 1, as shown in processing block 1451 is to enter a product, food or medication into the system. Step 2, as shown in processing block 1452 is to enter that product associated inventory of elements, nutrients and ingredients. Step 3, as shown in processing block 1453 is to enter the parameters of the subject into the system. Step 4, as shown in processing block 1454 is to generate a protocol valuation based on the previous steps. In Step 5, as shown in processing block 1455, the valuations are cross-referenced and matched. Finally in Step 6, as shown in processing block 1456, the products are scored and prioritized.

Figure 15A:
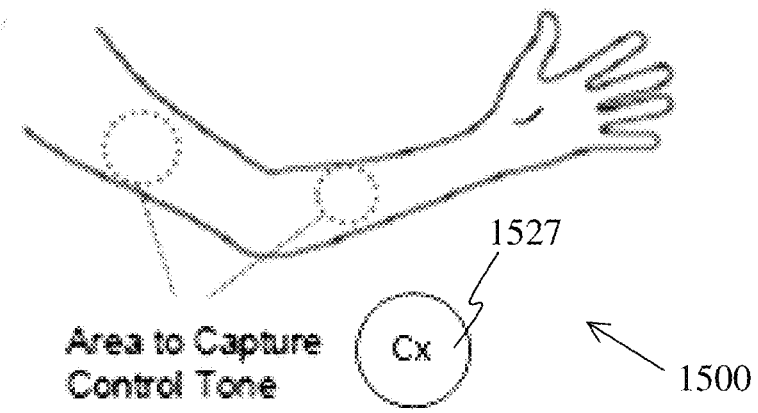
FIGS. 15A and 15B illustrate respectively, according to one embodiment of the PBVCES, a location example on the human body for capturing control tones, and applying a virtual tristimulus colorimeter (VTC) to facilitate the capture of a control tone.
Figure 15B:
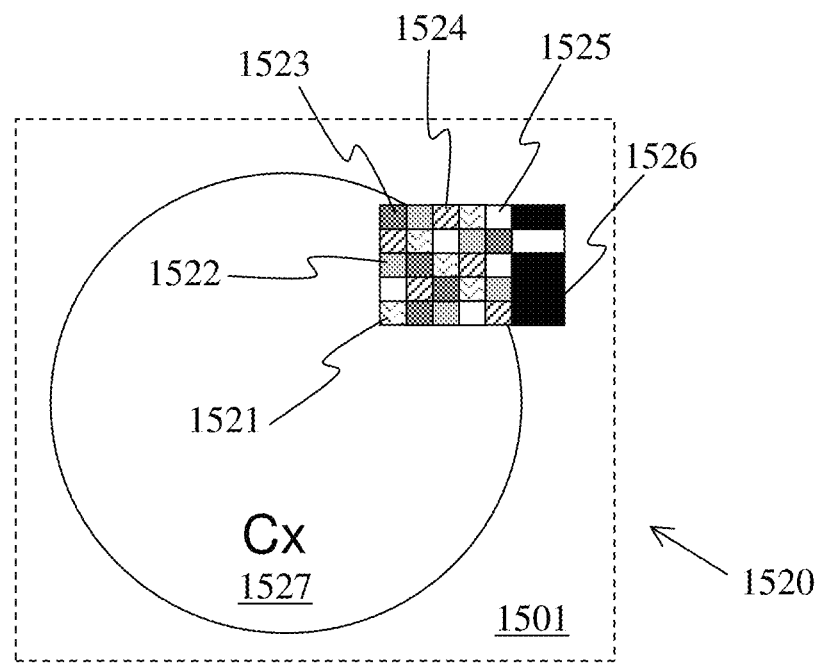

FIGS. 15A and 15B illustrate respectively, according to one embodiment of the PBVCES, a location example on the human body for capturing control tones 1500, and applying a virtual tristimulus colorimeter (VTC) 1520 to facilitate the capture of a control tone 1527. As illustrated in FIG. 15A, embodiments of the system may help identify the average skin tone or control tone (e.g. Cx 1527) of the subject. This can be done in some embodiments by taking an image of a skin area that has had minimal exposure to external factors which may have manipulated or altered its appearance over time, such as the sun for example. In some embodiments identifying the average skin tone or control tone 1527 may also comprise determining one or more hair color parameters and eye color parameters, applying a VTC 1520 and determining one or more Fitzpatrick skin type parameters. The Fitzpatrick skin type scale ranges from (i) for a pale ivory skin color, to (vi) for a very dark brown skin color. In FIG. 15B, one embodiment of applying a VTC 1520 is illustrated to facilitate the capture of a control tone 1527 and determining one or more Fitzpatrick skin type parameters. One embodiment of the VTC uses a 5-by-5 color grid with random permutations of five colors, 1521, 1522, 1523, 1524 and 1525. The grid may be printed at a specified size (i.e. height and width) and may optionally include one or more constant color 1526 (e.g. such as black or gray). Some embodiments of the grid may also be printed on or used in conjunction with a transdermal or medicated adhesive patch that is placed on the skin to deliver a specific dose of medication through the skin and into the bloodstream. For example in the grid illustrated, the color 1521 may correspond to yellow, color 1522 may correspond to green, color 1523 may correspond to blue, color 1524 may correspond to red, and color 1525 may correspond to white, or to a known reference shade of neutral gray (e.g. such as 18% gray) which may be used according to photographic techniques to adjust for various different lighting conditions and preserve consistency from image to image. Alternatively, a separate gray card may be used in some embodiments. An actual colorimeter may be used to determine and record the exact tristimulus values of these printed colors. Thereafter, such a VTC grid may be used to calibrate and/or correct measured skin tones, and to adjust for perspective distortions of size in the captured image 1501.

It will be appreciated that the skin region being analyzed to identify the average skin tone or control tone of the subject should ideally be free of topical applications and visible hair. But in an office visit, typically scheduled during working hours, clients may have already applied makeup, etc. Typically an office visit consultation may also include photographic and/or digital imagery, ultraviolet imagery, infrared or thermal imagery, etc. For example, accurate epidermal tristimulus color images may be captured by specialized hardware known as a colorimeter, which is designed to filter lighting sources to accurately provide tristimulus values. But embodiments of a VTC grid may be used to calibrate and/or correct measured skin tones, and to adjust for perspective distortions of size in a captured image, e.g. as taken by the client using a smartphone camera with a VTC application.

It will also be appreciated that integration of an atypical tone expert system can allow for identification, classification and measurement of discoloration tones outside the spectrum of standardized normal tones. Data from the system can be used to chart client progress and to prioritize supportive actions to address specified issues. The PBVCES provides for optimizing the predictive logic, by their registered professional users, to products and services considered most relevant and supportive in addressing the client's conditions, by adjusting a systematic process of classifying discolorations and calculating their severities. Thus in some embodiments, professional registered user may be provided with the ability to increase or to decrease temperature, redness value, and/or dark pigmentation ranges, etc. as parameters as a means to intensify points of concern or minimally isolate areas of concern, with flexibility based on the registered professional's preferences.

FIGS. 16A and 16B illustrate respectively, according to one embodiment of the PBVCES: color distance measurements, both in an example input-device color space 1600, and in an another alternative example color space 1605; and an example process flow of an image area analysis 1660.

As illustrated in FIG. 16A, in an example input-device color space 1600 a dermal image may be captured as a red-green-blue (RGB) image (e.g. image 1501). Thereafter, a VTC may be applied to calibrate and/or correct measured skin tones, and to adjust for perspective distortions of size in the captured image. In some embodiments a color distance, $D_{RGB}$, may be calculated in similarity to a 3D Euclidean distance as:

$$D_{RGB} = \sqrt{(R2-R1)^2 + (G2-G1)^2 + (B2-B1)^2}.$$

In other words, the distance 1640 may be calculated as the square-root of the sum of the distance 1610 squared plus the distance 1620 squared plus the distance 1630 squared. It may often be acceptable to also omit the square-root calculation.

Although a standard RGB input-device color space 1600 (i.e. where R is sampled at 700 nm, G is sampled at 546.1 nm, and B is sampled at 435.8 nm) is convenient, especially from a hardware perspective, there are many other well-established color spaces and well-established color distances. For example, the Commission Internationale d'Eclairage (1931) defined a standard system (CIE-XYZ) for color representation, wherein Y was chosen to equal the luminance of monochromatic light (essentially black-and-white or grayscale). The CIE-XYZ system for color representation is illustrated as color space 1650. A color distance, $D_{XYZ}$, may also be calculated in similarity to a 3D Euclidean distance as:

$$D_{XYZ} = \sqrt{(X2-X1)^2 + (Y2-Y1)^2 + (Z2-Z1)^2}.$$

In other words, the distance 1645 may be calculated as the square-root of the sum of the distance 1615 squared plus the distance 1625 squared plus the distance 1635 squared.

It will be appreciated that the distance, $D_{RGB}$, in color space 1600 will not, in general, be equal to the distance, $D_{XYZ}$, in color space 1650. Moreover, the choice of primaries typically reflects a preference for matching hardware capabilities in camera sensors, printers, monitors and film with the bell curves representative of human visual perception. Thus a cyan-magenta-yellow (CMY) subtractive color space is typically used in color photography, and a cyan-magenta-yellow-black (CMYB) subtractive color space is typically used in color printing. But a YIQ or $YC_bC_r$ (which stand for luminance, Y; blue chrominance, $C_b$ or Q; and red chrominance, $C_r$ or I) color space is typically used for color television and color image compression, while a hue-lightness-saturation (HLS) may be used for human interactive painting. In any event, distance calculations may be weighted in any of these color spaces in order to achieve a desired effect.

It will also be appreciated that there is no inherent reason to limit the choice of color spaces to just three dimensions, nor to just the visible spectrum. It is certainly within the scope of this disclosure that a dermal image may be captured, for example as a red-green-blue-infrared (RGBIR) image by a smartphone camera, or as a red-green-blue-ultraviolet (RGBUV) image, for example as captured by an attachment to a smart device for using ultraviolet light exposure and/or ultraviolet lens filtering, and that a proprietary color space and/or one or more of a variety of metrics may be selected to improve the detection and/or measurement of various dermal or epidermal properties including but not limited to: heat and redness associated with inflammation, cold or blueness associated with lack of circulation, bilirubin levels associated with itchiness, luminance differences associated with disparity in pigmentation, etc.

It will be appreciated that in some embodiments, compatibility may be established, e.g. as one or more compatibility modes, providing for translations between color spaces, black and white, grey-scale, ultraviolet, infrared or thermal, etc., e.g. in a manner similar to the compatibility between color television broadcast signals and black and white television broadcast signals. In alternative embodiments, compatibility modes may be established for specialized color spaces, e.g. to measure redness, heat, yellowness, bruising, etc., and such specialized compatibility modes may be selected for use, e.g. in the expert system analysis, by registered professionals. In some alternative embodiments, compatibility may be established with colors invisible to the human eye, such as ultraviolet, e.g. using its smaller wavelengths to penetrate through a top layer of the skin but bounce off an inner more-dense layer.

As in the example illustrated in FIG. 16B, once the image is captured, a range for the average tone of the region may be calculated, for example from the color values of the captured areas 1527. This color value is known as a control tone.

Once a control tone has been established, it may then be converted into black and white, or grey-scale values, e.g. in accordance with one or more compatibility modes, in some embodiments. The next step may then be to take an image of the skin area being evaluated. In some embodiments, the goal of a system process such as this may not even be to diagnose or to treat a condition, but may instead be simply to evaluate the atypical tonal values and calculate the ratio of severity when compared to a control tone based on conditional parameters. These atypical light tones and/or atypical dark tones of an appearance, condition or concern may then, in some embodiments, have completely different support prioritization based on the ratio of severity.

Once the image is captured, it may also be converted into defined colors, e.g. C1-C8 found within the image, with corresponding area percentages as shown in table 1661. These colors may also then be translated into grey shades, e.g. where lighter shades may be represented by smaller values (such as the value of 3 associated with G5) and darker shades may be associated with larger values (such as the value of 58 associated with G4) and organized from light to dark with their corresponding area percentages as shown in tables 1662 and 1663. The shades within the range of the control tone may be filtered or removed, which in this example corresponds to regions identified with G1, G2, and G6 and represents the translated grey-scale values of 36% of the imaged skin, thereby leaving only tones that are either lighter (e.g. region G5) or darker (e.g. regions G3, G8, G7 and G4) than the control tone. This process may be a crucial part of the system in some embodiments. Atypical characteristics will usually be lighter or darker than the average skin tone. After analysis, the severity ratio of the atypical tones for that particular image may be determined e.g. as: 6% atypically light; 36% within the range of control tones; and 36% atypically dark.

FIG. 17 illustrates, according to one embodiment of the PBVCES, a valuation wheel and logic 1700 of atypical tone mapping graphics. At step 1, as shown in processing block 1732: through the protocol valuation technique, a prioritization of support 1781 is created. At step 2, as shown in processing block 1760: tones designated as control tones in table 1762 are not distributed into sections of the valuation wheel 1782. At step 3, as shown in processing block 1761: the remaining atypical tones in table 1763 are distributed into sections of the valuation wheel 1783 by matching color percentages with priority values with the highest percentage in priority category 1 and succession from there on.

Figure 18:
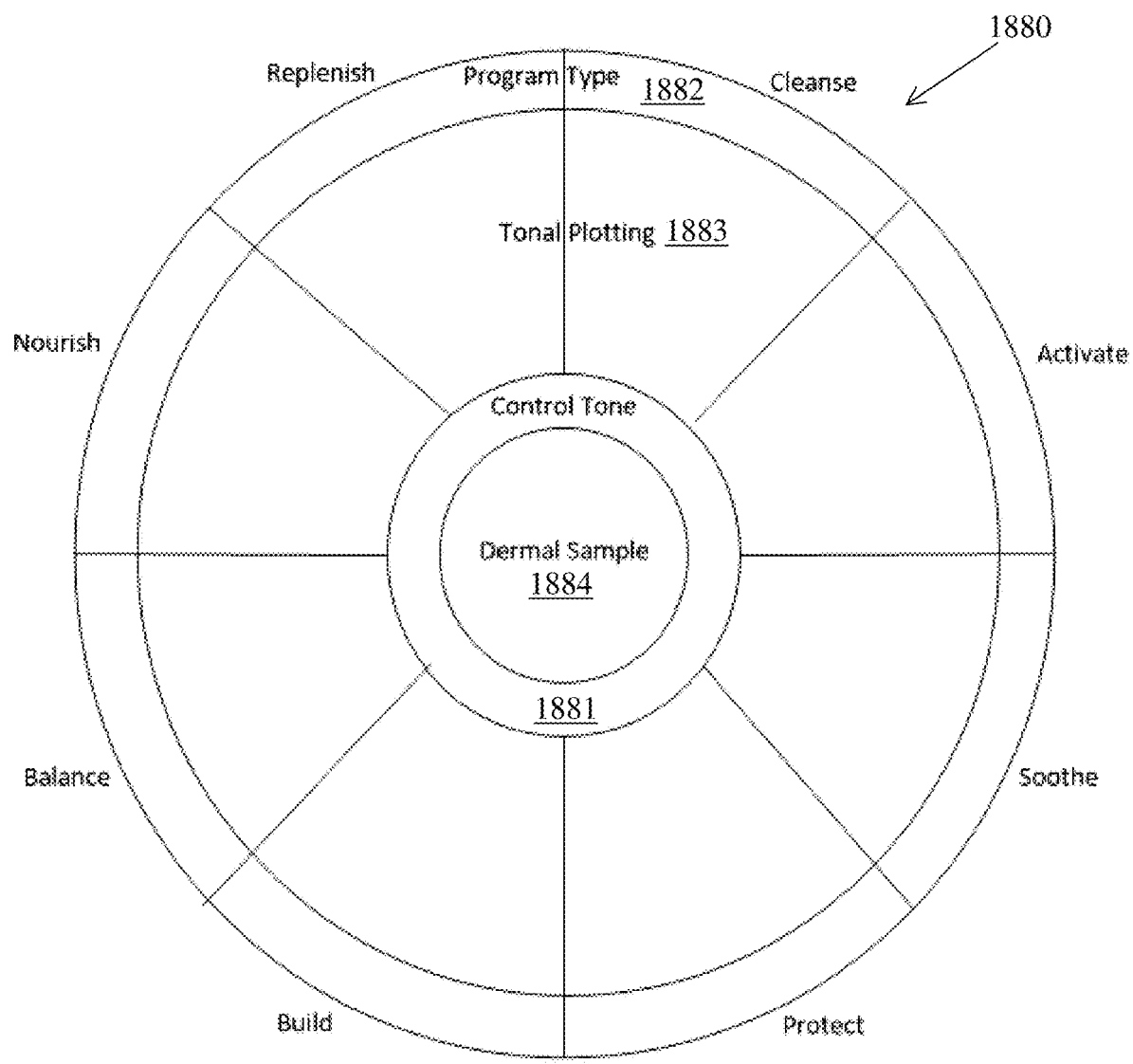
FIG. 18 illustrates, according to one embodiment of the PBVCES, a valuation wheel as a tool to graphically reference health, wellness and skincare data.

FIG. 18 illustrates, according to one embodiment of the PBVCES, a valuation wheel 1880 as a tool to graphically reference health, wellness and skincare data. The valuation wheel 1880 comprises a tool to graphically reference data captured via the PBVCES platform. For example, valuation wheel 1880 may be derived from a control tone 1881, program type 1882, tonal plotting 1883 and an image of a dermal sample 1884. The valuation wheel control tone is determined by the image collected of an unexposed area of the average skin tone of a particular person. For example, unexposed may be defined as an area that has had minimal exposure to external factors-such as the sun, which otherwise would have likely manipulated or altered its appearance over time. It also requires an area clear of blemishes and/or hair.

As illustrated in FIG. 15A, an ideal location 1500 is the underarm, such as between the biceps and triceps, or under-forearm region. This averaged tone or control tone 1881 (e.g. Cx 1527) may be utilized as a calibration to calculate the spectrum of colors to consider. People of diverse ethnicity, and skin tones, have different types of discolorations based on appearance concerns and conditions. For example, the Fitzpatrick skin type scale ranges from (i) for a pale ivory skin color, to (vi) for a very dark brown skin color. In some embodiments identifying the average skin tone 1527 or control tone 1881 may also comprise determining one or more hair color parameters and eye color parameters, applying a VTC 1520 and determining one or more Fitzpatrick skin type parameters. Therefore, different templates of colors and/or color spaces may need to be considered based on the average skin tone 1527 of each individual. Another reason that control tone 1881 is important is to determine typical from atypical as a filtering mechanism for plotting tones into the sections. All colors of a dermal image may be passed through the control tone 1881 as a filter, e.g. in some embodiments by computing a color distance, $D_{RGB}$, in similarity to a 3D Euclidean distance. In some alternative embodiments, the color distance may be computed within another alternative color space, e.g. which may be selected based on said one or more Fitzpatrick skin type parameters. Tones consistent with the control tone, within a small degree of variation, may be considered normal. If the tone is different, it is passed through said control tone 1881 filter and placed into the appropriate section based on tonal assignment. It will also be appreciated that while specific examples are shown herein using images of skin tones, or thermal images, other types of images may also be used (e.g.

x-rays, magnetic resonance imaging scans, ultrasound scans, computed tomography scans, positron emission tomography scans, molecular imaging, etc.) without departing from the broader teachings of the invention.

Embodiments of valuation wheel 1880 may have a program type comprised of eight sections, listed as cleanse, soothe, protect, balance, nourish, replenish, activate and build, as identified by objectives. The program type listed objectives can represent a categorization system to encompass the most accepted ways to support health, wellness and appearance goals. Each support objective may have an archived inventory of topical skincare ingredients, nutritional micronutrients and macronutrients and supplemental ingredients. Each nutrient may be archived in a section based on cited supportive properties. An ingredient can have numerous properties and therefore may be listed in more than just one section. Embodiments of valuation wheel tonal plotting 1883 contain extracted colors which may be filtered, e.g. through the control tone 1881 as described above, to highlight the full range of atypical tones defined as discolorations. Each discoloration tone may be given a conditional value (e.g. a color distance, $D_{RGB}$, in similarity to a 3D Euclidean distance) and then categorically assigned into one of eight possible sections. The section in which tones are placed may be predetermined during the calibration process, e.g. as described above. In some embodiments, the more populated a section is with assigned tones, the more emphasis may be associated with a corresponding objective. Embodiments of a valuation wheel 1880 dermal image uploaded for the control tone 1881 and for the dermal image sample 1884 for analysis may be positioned here.

In prior art systems, consultation with a dermatologist or other skin-care professional may include an office visit and examination, and may also potentially include photographic and/or digital imagery, infrared imagery, etc. But since an office visit is typically scheduled during working hours, clients may come from their own working environment, so the skin region being analyzed may not be free of topical applications as clients may have already applied makeup, etc. Such images may require high resolution and consistent lighting, e.g. accurate epidermal tristimulus color images captured by specialized hardware known as a tristimulus colorimeter, designed to filter lighting sources to accurately provide tristimulus values. Frequent office visits and examinations may also become prohibitively expensive, proscribed by insurers, and/or difficult to schedule into the busy day-to-day routines of both professionals and clients.

Implementation by the client of the prescribed treatments, continued monitoring of treated areas by the professional, engagement between the professional and client during the implementation and adjustments to the prescribed treatments, may be crucial to the success of any such course of treatments. Human motivation levels can vary significantly as related to the specified time-period considered necessary to achieve an identified goal. Acquisition of new habits necessary for maintaining long term success may also be hindered by barriers that interfere with an effective, efficient and continuous engagement process. These factors can contribute to protracted time requirements for achieving a successful treatment result, and so increase the long-term likelihood of failure.

It will be appreciated that integration of PBVCES processes, e.g. such as a VTC implementation in a smartphone, a web-based atypical tone expert system, a graphical valuation tool such as the valuation wheel, etc., can allow for identification, classification and measurement of discoloration tones; continued monitoring of treated areas, engagement between the professional and client, and adjustments to the prescribed treatment plan.

Thus integration, in one embodiment, of these various proprietary PBVCES processes as a platform comprising: smartphone apps, web-based or cloud-based B2C data reporting, B2B portals, warehouses, knowledge bases, connected devices, expert systems and APIs, etc.; is intended through use of dedicated hardware, software an/or firmware executable by general purpose computers, servers and phones, and/or by special purpose machines or by combinations of the above.

FIGS. 19A, 19B, 19C and 19D illustrate alternative flow diagrams 1901-1904 for various example embodiments of proprietary PBVCES processes. Processes 1901-1904 and other processes herein disclosed are performed by processing blocks that may comprise dedicated hardware or software or firmware operation codes executable by general purpose machines or by special purpose machines or by a combination of both.

Figure 19A:
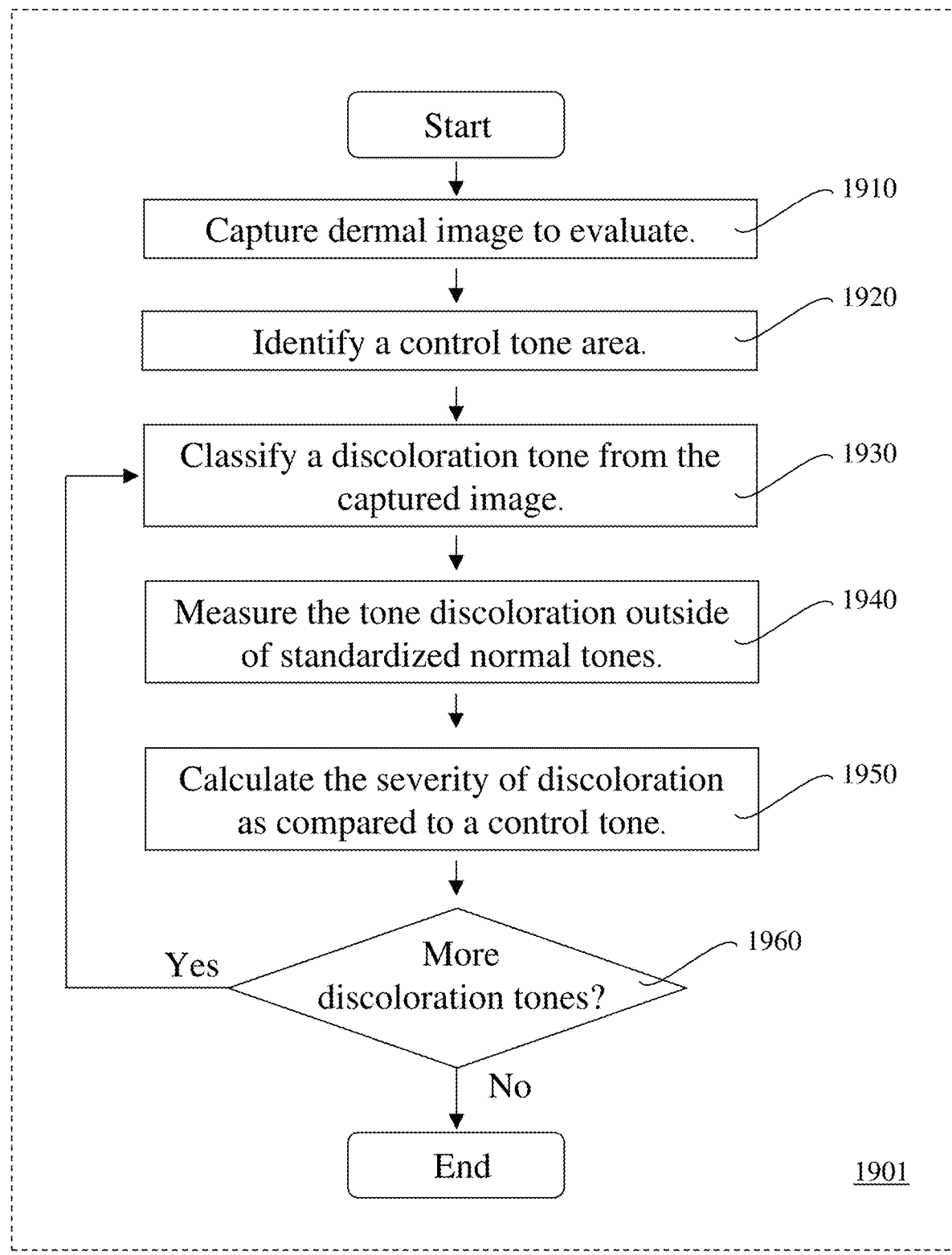
FIGS. 19A, 19B, 19C and 19D illustrate alternative flow diagrams for various example embodiments of proprietary PBVCES processes.

As illustrated in FIG. 19A processing starts, in at least one embodiment of process 1901 for mapping atypical skin discoloration, at processing block 1910 where a dermal image of the skin area of a user to be evaluated is captured, e.g. by a cell phone camera. In processing block 1920, a control tone area of a user is identified, e.g. based on conditional parameters. Next in processing block 1930, discoloration tones from captured dermal images are classified. In processing block 1940, discoloration tones outside the spectrum of standardized normal tones are measured, e.g. by calculating a conditional value for a color distance, $D_{RGB}$, in similarity to a 3D Euclidean distance, but it will be appreciated that other distance metrics in various color spaces may be used. In processing block 1950, severity of tone discoloration when compared to a control tone, e.g. in some embodiments as a ratio and/or a percentage, is calculated, in one embodiment based on conditional parameters. In processing block 1960, a determination is made as to whether or not there are any more discoloration tones left to process when compared to the control tone. If so, then processing reiterates beginning in processing block 1930. Otherwise process 1901 ends after processing block 1960.

Figure 19B:
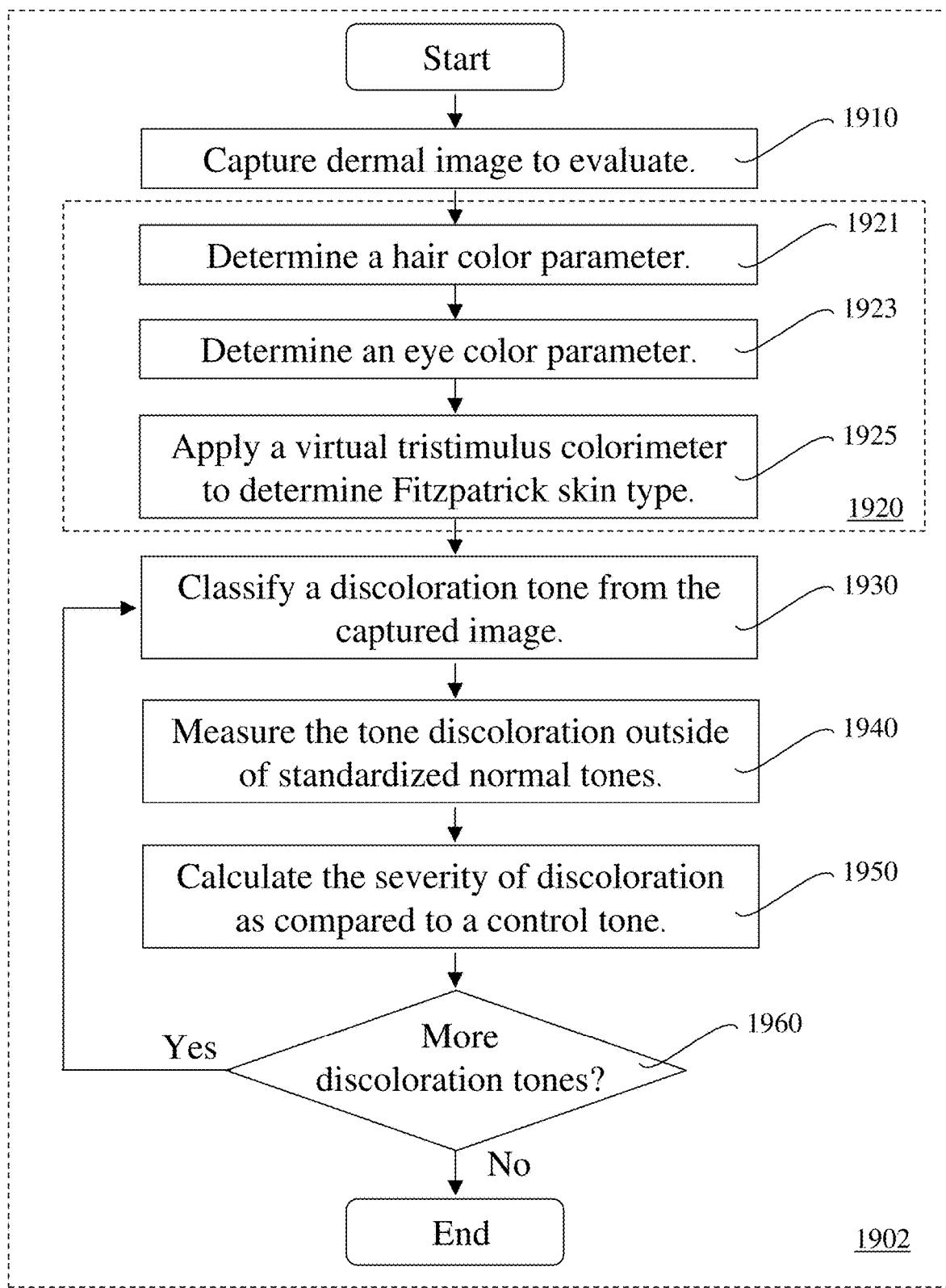

As illustrated in FIG. 19B processing starts, in at least one alternative embodiment of process 1902 for mapping atypical skin discoloration, at processing block 1910 wherein a dermal image of the skin area of a user to be evaluated is captured, e.g. by a cell phone camera. In processing block 1921 of process 1920 wherein a control tone area of the user is to be identified, one or more hair color parameters may be determined. In processing block 1923 one or more eye color parameters may be determined. In processing block 1925 a virtual tristimulus colorimeter is applied in order that one or more Fitzpatrick skin type parameters may be determined as part of process 1920 in identifying the control tone area of the user. Next in processing block 1930, discoloration tones from captured dermal images are classified. In processing block 1940, discoloration tones outside the spectrum of standardized normal tones are measured and/or evalueated, e.g. by calculating one or more color distance metrics in one or more selected color spaces. In processing block 1950, severity of tone discoloration when compared to a control tone is calculated, in one embodiment based on conditional parameters. Then in processing block 1960, a determination is made as to whether or not there are any more discoloration tones left to process when compared to the control tone. If so, then processing reiterates beginning in processing block 1930. Otherwise process 1902 ends after processing block 1960.

Figure 19C:
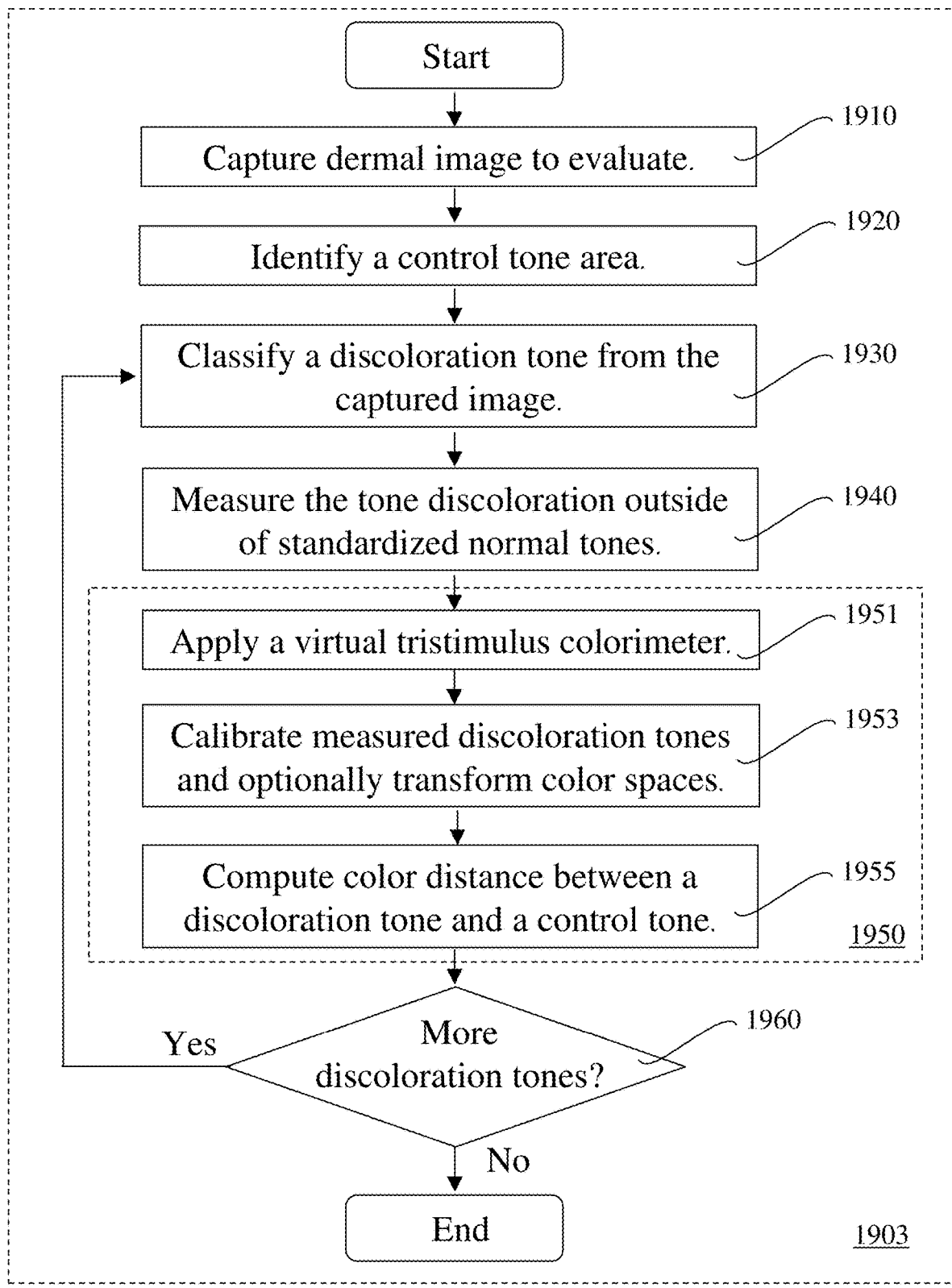

As illustrated in FIG. 19C processing starts, in at least one embodiment of process 1903 for mapping atypical skin discoloration, at processing block 1910 where a dermal image of the skin area of a user to be evaluated is captured, e.g. by a cell phone camera. In processing block 1920, a control tone area of a user is identified, e.g. based on conditional parameters. Next in processing block 1930, discoloration tones from captured dermal images are classified. In processing block 1940, discoloration tones outside the spectrum of standardized normal tones are measured, e.g. by calculating a conditional value for a color distance, $D_{XYZ}$, in similarity to a 3D Euclidean distance, but it will be appreciated that other distance metrics in various color spaces may be used. In processing block 1951 of process 1950 wherein severity of tone discoloration when compared to a control tone is calculated, a virtual tristimulus colorimeter is applied. In processing block 1953 the measured discoloration tones are calibrated, and optionally in some embodiments a color space transformation may be performed for the calibrated discoloration tones and/or the identified control tone. In processing block 1955 one or more color distances between the calibrated discoloration tones and the identified control tone are computed as part of process 1950 in calculating the severity of tone discolorations when compared to the control tone. In embodiments where a color space transformation may be performed for the discoloration tones and/or the identified control tone, it will be appreciated that the color space transformation may be performed before computing said one or more color distances. In processing block 1960, a determination is made as to whether or not there are any more discoloration tones left to process when compared to the control tone. If so, then processing reiterates beginning in processing block 1930. Otherwise process 1903 ends after processing block 1960.

Figure 19D:
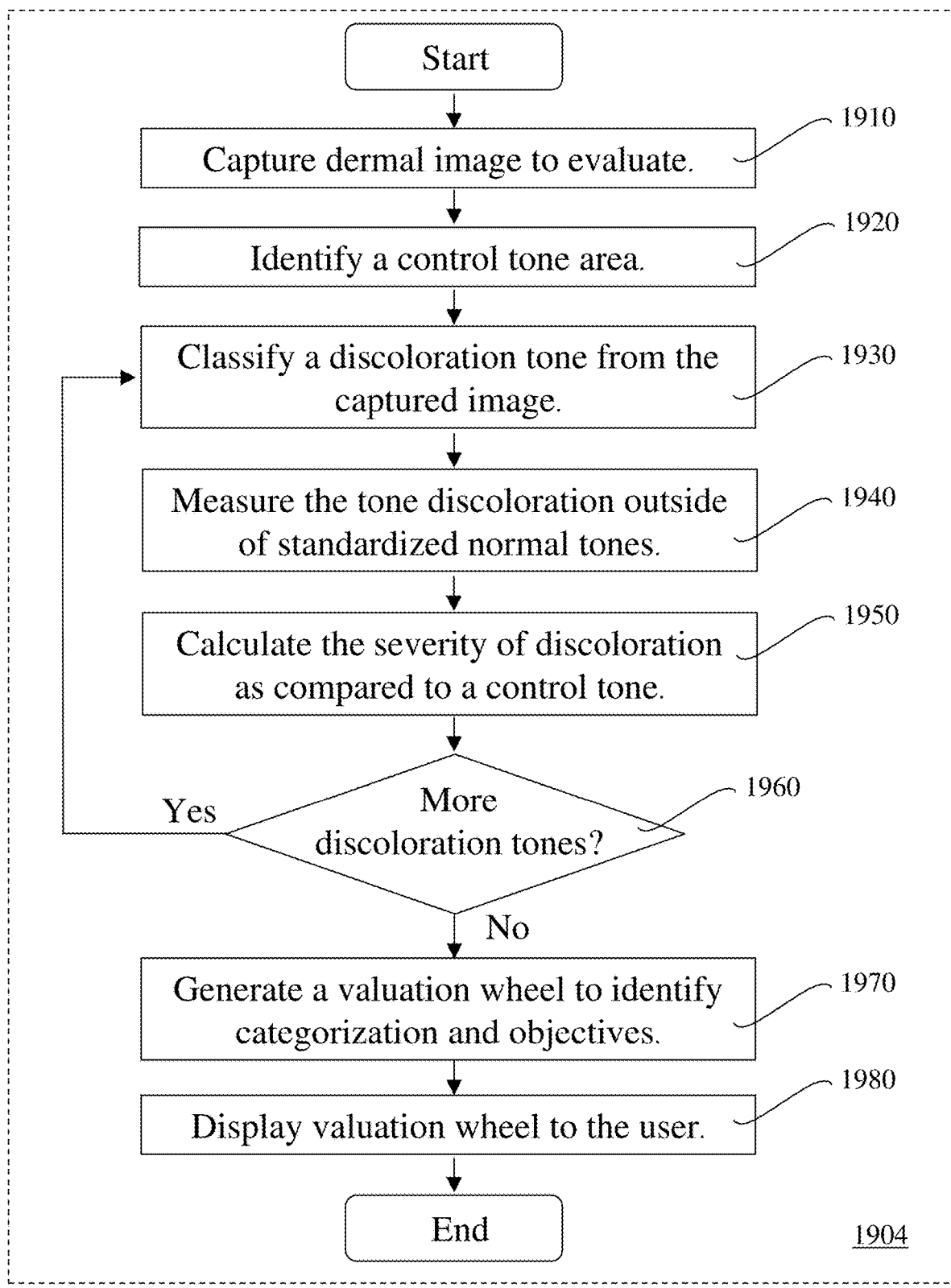

As illustrated in FIG. 19D processing starts, in at least one embodiment of process 1904 for mapping atypical skin discoloration, at processing block 1910 where a dermal image of the skin area of a user to be evaluated is captured, e.g. by a cell phone camera. In processing block 1920, a control tone area of a user is identified, e.g. based on conditional parameters. Next in processing block 1930, discoloration tones from captured dermal images are classified. In processing block 1940, discoloration tones outside the spectrum of standardized normal tones are measured, e.g. by calculating a conditional value for a color distance, $D_{RGBI}$, in similarity to a 4D Euclidean distance, but it will be appreciated that other distance metrics in various color spaces may be used. In processing block 1950, severity of tone discoloration when compared to a control tone, e.g. in some embodiments as a ratio and/or a percentage, is calculated, in one embodiment based on conditional parameters. In processing block 1960, a determination is made as to whether or not there are any more discoloration tones left to process when compared to the control tone. If so, then processing reiterates beginning in processing block 1930. Otherwise in processing block 1970 a valuation wheel for display to a user is generated based on the calculated ratio of severity of tone discoloration when compared to the control tone. In some embodiments the valuation wheel may identify a categorization system with multiple objectives, one or more captured dermal sample, tonal plotting and one or more control tone. Then in processing block 1980 the valuation wheel may be displayed to the user that visually depicts relationships between health, wellness and skincare data in reference to atypical skin discoloration, and process 1904 ends after processing block 1980.

It will be appreciated that processing blocks illustrated as being executed in a particular order may also be executed in another order, or concurrently, or in parallel with each other, if possible in some alternative embodiments of processes 1901-1904 and in any other processes herein disclosed. Embodiments of the mechanisms disclosed herein may be implemented in hardware, software, firmware, or a combination of such implementation approaches. Embodiments of the invention may be implemented as computer programs or program code executing on programmable systems comprising at least one processor, a storage system (including volatile and non-volatile memory and/or storage elements), at least one input device, and at least one output device.

Embodiments of a PBVCES platform are disclosed above to remotely measure dermal and epidermal properties with precision and to enhance decision-making through expert diagnostic and predictive services. Embodiments mapping atypical skin discoloration may include capture means for capturing dermal images of the skin area of a user to be evaluated; control means for identifying the control tone area of a user based on conditional parameters; classification means for classifying the discoloration tones from captured dermal images; measurement means for measuring discoloration tones outside the spectrum of standardized normal tones; and quantification means for calculating the ratio of severity of tone discoloration when compared to a control tone based on conditional parameters. In some embodiments a dermal image may be captured as a red-green-blue (RGB) image. Embodiments of a VTC grid may be used to calibrate and/or correct measured skin tones, and to adjust for perspective distortions of size in a captured image, e.g. as taken by the client using a smartphone camera with a VTC application. In some embodiments a color distance, $D_{RGB}$, may be calculated in similarity to a 3D Euclidean distance. It will also be appreciated that there is no inherent reason to limit the choice of color spaces to just three dimensions, nor to just the visible spectrum. In some embodiments a dermal image may be captured, for example as a red-green-blue-infrared (RGBI) image by a smartphone camera, and in a proprietary color space and/or using one or more of a variety of metrics selected to improve the detection and/or measurement of various dermal or epidermal properties including but not limited to: heat and redness associated with inflammation, cold or blueness associated with lack of circulation, bilirubin levels associated with itchiness, luminance differences associated with disparity in pigmentation, etc. In some embodiments, one or more compatibility modes may be established, providing for translations between color spaces, black and white, grey-scale, or for specialized color spaces, e.g. to measure redness, heat, yellowness, bruising, etc., and such specialized compatibility modes may be selected for use in expert system analysis by registered professional users.

While only selected embodiments have been chosen to illustrate the present invention, it will be apparent to those skilled in the art from this disclosure that various changes and modifications can be made without departing from the scope of the invention as defined in the appended claims. Furthermore, the foregoing descriptions of the embodiments according to the present invention are provided for illustration only, and not for the purpose of limiting the invention as defined by the appended claims. In an area of technology such as this, where growth is fast and further advancements are not easily foreseen, the disclosed embodiments may be readily modifiable in arrangement and detail as facilitated by enabling technological advancements without departing from the principles of the present disclosure or the scope of the accompanying claims.

What is claimed is:

1. A method for virtual tristimulus colorimetry comprising:
   recording a color grid including one or more permutations of a plurality of predetermined colors;
   recording a scale of the color grid as being printed or projected at a predetermined size;
   applying a virtual tristimulus colorimeter to a first image; and
   recording a result comprising a second image calibrated from the first image according to the virtual tristimulus colorimeter,
   wherein said scale is used to adjust distortions of size in the recorded second image.

2. The method according to claim 1, wherein said color grid comprises a 5-by-5 grid with a pseudorandom permutation of 5 colors.

3. The method according to claim 2, wherein said color grid comprises one or more constant colors.

4. The method according to claim 3, wherein a first constant color of said one or more constant colors is gray.

5. The method according to claim 4, wherein said first constant color is 18% gray.

6. The method according to claim 1, wherein said color grid is printed at a predetermined size on a transdermal or medicated adhesive patch.

7. The method according to claim 1, wherein an actual colorimeter is used to predetermine the plurality of colors to record for said color grid.

8. The method according to claim 1, wherein said scale is used to adjust for perspective distortions of size in the recorded second image.

9. The method according to claim 1, wherein the first image is captured using a smartphone camera.

10. The method according to claim 9, wherein the smartphone camera has a virtual tristimulus colorimeter smartphone application.

11. A non-transitory machine-readable medium to record functional descriptive material including one or more executable instructions, which if executed by one or more machines causes the machine to:
    record a color grid including one or more permutations of a plurality of predetermined colors;
    record a scale of the color grid as being printed or projected at a predetermined size;
    apply a virtual tristimulus colorimeter to an image; and
    record a result comprising the image calibrated according to the virtual tristimulus colorimeter,
    wherein said scale is used to adjust distortions of size in the calibrated image of the recorded result.

12. The non-transitory machine-readable medium according to claim 11, wherein said color grid comprises a 5-by-5 grid with a pseudorandom permutation of 5 colors.

13. The non-transitory machine-readable medium according to claim 11, wherein said color grid comprises one or more constant colors including a gray color.

14. The non-transitory machine-readable medium according to claim 11, wherein the image is captured using a smartphone camera and a virtual tristimulus colorimeter smartphone application.

15. The non-transitory machine-readable medium according to claim 11, wherein said scale is used to adjust for perspective distortions of size in the recorded image.

16. A system for virtual tristimulus colorimetry comprising:
    a capture device to capture one or more dermal images of one or more skin areas of a user;
    a color grid including one or more permutations of a plurality of recorded predetermined colors;
    a recorded scale of the color grid as being printed or projected at a predetermined size;
    an application of the virtual tristimulus colorimeter to an image; and
    a result of the application comprising an image result calibrated according to the virtual tristimulus colorimeter,
    wherein said scale is used to adjust distortions of size in the calibrated image result.

17. The system according to claim 16, wherein said capture device comprises a smartphone camera.

18. The system according to claim 16, wherein said capture device comprises a smart device for ultraviolet light exposure.

19. The system according to claim 16, wherein said capture device comprises a smart device for infrared light exposure.

20. The system according to claim 16, wherein said capture device comprises a virtual tristimulus colorimeter smartphone application.

21. The system according to claim 16, wherein a first image of said one or more dermal images comprises a red-green-blue digital image.

22. The system according to claim 20, wherein the first image of said one or more dermal images is captured as a red-green-blue-ultraviolet digital image.

23. The system according to claim 20, wherein the first image of said one or more dermal images is captured as a red-green-blue-infrared digital image.

* * * * *